United States Patent
Gravestock et al.

(10) Patent No.: US 7,157,482 B2
(45) Date of Patent: Jan. 2, 2007

(54) ANTIBACTERIAL 1,3-OXAZOLIDIN-2-ONE DERIVATIVES

(75) Inventors: Michael Barry Gravestock, Waltham, MA (US); Neil James Hale, Macclesfield (GB); Sheila Irene Hauck, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/550,039

(22) PCT Filed: Mar. 16, 2004

(86) PCT No.: PCT/GB2004/001119

§ 371 (c)(1),
(2), (4) Date: Sep. 21, 2005

(87) PCT Pub. No.: WO2004/083205

PCT Pub. Date: Sep. 30, 2004

(65) Prior Publication Data

US 2006/0084810 A1    Apr. 20, 2006

(30) Foreign Application Priority Data

Mar. 20, 2003 (GB) ................................. 0306358.3

(51) Int. Cl.
| | |
|---|---|
| *A01N 43/76* | (2006.01) |
| *A01N 43/72* | (2006.01) |
| *A01N 43/828* | (2006.01) |
| *A01N 43/647* | (2006.01) |
| *A01N 43/56* | (2006.01) |
| *C07D 261/06* | (2006.01) |
| *C07D 263/04* | (2006.01) |

(52) U.S. Cl. ...................... 514/376; 514/359; 514/403; 514/372; 514/378; 514/361; 548/229; 548/255; 548/247; 548/206; 548/364.1

(58) Field of Classification Search ................ 514/359, 514/372, 378, 361, 406; 548/364.1, 247, 548/255, 206
See application file for complete search history.

(56) References Cited

FOREIGN PATENT DOCUMENTS

| EP | 0352 781 A2 | 1/1990 |
|---|---|---|
| EP | 0352 781 A3 | 1/1990 |
| WO | WO 99/64416 A2 | 12/1999 |
| WO | WO 99/64416 A3 | 12/1999 |
| WO | WO 01/81350 A1 | 11/2001 |
| WO | WO 02/081470 A1 | 10/2002 |
| WO | WO 03/035648 | 5/2003 |
| WO | WO 03/072575 | 9/2003 |
| WO | WO 03/072576 A2 | 9/2003 |
| WO | WO 03/072576 A3 | 9/2003 |

*Primary Examiner*—Joseph K. McKane
*Assistant Examiner*—Yong Chu

(57) ABSTRACT

Compounds of the formula (I), or a pharmaceutically-acceptable salts, or in-vivo-hydrolysable esters thereof, wherein: N—HET is for example triazolyl substituted with $R^1$; $R^1$ is for example optionally substituted (1-4C)alkyl; Q is for example phenyl or pyridyl, substituted with T; T is for example selected from (TAa1 to TAa12) such as (TAa1 and TAa5); formula (II): $R^{4h}$, $R^{5h}$, $R^{6h}$ are for example selected from hydrogen, (1-4C)alkyl, (1-4C)alkoxycarbonyl, (1-4C) alkanoyl and carbamoyl; processes for making them, compositions containing them and their use as antibacterial agents are described.

8 Claims, No Drawings

ANTIBACTERIAL 1,3-OXAZOLIDIN-2-ONE DERIVATIVES

CROSS-REFERENCE TO RELATED APPLICATIONS

This application is a US National Stage under 35 U.S.C. § 371 of International Application No. PCT/GB2004/001119 (filed Mar. 16, 2004) which claims priority under 35 U.S.C. § 119(a)–(d) to Application No. GB 0306358.3, filed on Mar. 20, 2003, the specification of which is incorporated by reference herein.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as principally effective against Gram-positive pathogens.

Gram-positive pathogens, for example Staphylococci, Enterococci, and Streptococci are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Certain antibacterial compounds containing an oxazolidinone ring have been described in the art (for example, Walter A. Gregory et al in J. Med. Chem. 1990, 33, 2569–2578 and Chung-Ho Park et al in J. Med. Chem. 1992, 35, 1156–1165). Such antibacterial oxazolidinone compounds with a 5-acetamidomethyl side-chain may be subject to mammalian peptidase metabolism. Furthermore, bacterial resistance to known antibacterial agents may develop, for example, by (i) the evolution of active binding sites in the bacteria rendering a previously active pharmacophore less effective or redundant, (ii) the evolution of means to chemically deactivate a given pharmacophore and/or (iii) the development and/or up-regulation of efflux mechanisms. Therefore, there remains an ongoing need to find new antibacterial agents with a favourable pharmacological profile, in particular for compounds containing new pharmacophores.

Additionally, certain antibacterial compounds containing an oxazolidinone ring have activity against the enzyme mono-amine oxidase (MAO), for instance compounds with amidomethyl or hydroxymethyl side chains at C-5 of the oxazolidinone ring. This may potentially lead to undesirable properties such as elevation in blood pressure when administered to a patient, or potentially cause drug-drug interactions. Therefore, there remains an ongoing need to find new antibacterial agents of the oxazolidinone class with a more favourable profile against MAO.

We have discovered a new class of antibiotic compounds containing an oxazolidinone ring substituted by a 5-azolylmethyl moiety in which the azole group is linked via a nitrogen atom and is itself further substituted. These compounds have particularly useful activity against Gram-positive pathogens including MRSA and MRCNS and, in particular, against various strains exhibiting resistance to vancomycin and against *E. faecium* strains resistant to both aminoglycosides and clinically used β-lactams. The compounds of the invention also show a favourable, decreased, MAO potency compared with other oxazolidinone analogues, for example those with an unsubstituted 5-azolylmethyl moiety, from the prior art.

Accordingly the present invention provides a compound of the formula (I), or a pharmaceutically-acceptable salt, or an in-vivo-hydrolysable ester thereof,

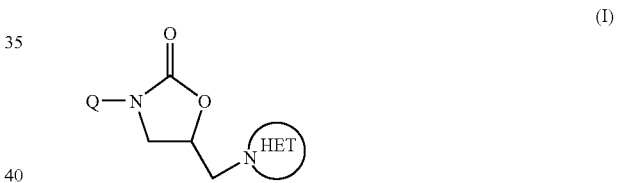

(I)

wherein —N—HET is selected from the structures (Ia) to (If) below:—

(Ia)

(Ib)

(Ic)

(Id)

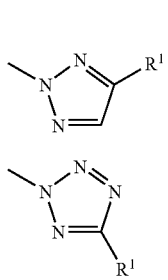

(Ie)

(If)

wherein u and v are independently 0 or 1;

R¹ is (1-4C)alkyl;

or R¹ is selected from a substituent from the group
(R¹a) wherein R¹ is halogen, hydroxy, (1-4C)alkoxy, (2-4C)alkenyloxy, (2-4C)alkenyl, (2-4C)alkynyl (optionally substituted on the terminal carbon by $CH_2=CH-$, di(1-4C)alkylamino, AR2, AR2a or AR2b, wherein AR2, AR2a and AR2b are defined hereinbelow), (3-6C)cycloalkyl, (3-6C)cycloalkenyl, amino, (1-4C)alkylamino, di-(1-4C)alkylamino, (2-4C)alkenylamino, (1-4C)alkyl-S(O)q- (wherein q is 0, 1 or 2), (1-4C)alkylcarbonylamino, ;

or R¹ is selected from the group
(R¹b) wherein R¹ is a (1-4C)alkyl group which is substituted by one substituent selected from hydroxy, halo, (1-4C)alkoxy, amino, (1-4C)alkylamino, di(1-4C)alkylamino, cyano, azido, (2-4C)alkenyloxy, (1-4C)alkyl-S(O)q- (wherein q is 0, 1 or 2), AR1-S(O)q- (wherein q is 0, 1 or 2 and AR1 is defined hereinbelow), AR2-S(O)q- (wherein q is 0, 1 or 2), AR2a -S(O)q- (where q is 0, 1 or 2), benzyl-S(O)q- (wherein q is 0, 1 or 2), (3-6C)cycloalkyl, (3-6C)cycloalkenyl, (1-4C)alkyl-OCO—NH—, (1-4C)alkyl-NHCO—O—, (1-4C)alkylaminocarbonyl, di(1-4C)alkylaminocarbonyl, $H_2NC$(=NH)S—;

or R¹ is selected from a group of formula (R¹c1):—
(R¹c1) a fully saturated 4-membered monocyclic ring containing 1 or 2 heteroatoms independently selected from O, N and S (optionally oxidised), and linked via a ring nitrogen or carbon atom; or or R¹ is selected from the group
(R¹d) cyano, nitro, azido, formyl, (1-4C)alkylcarbonyl, (1-4C)alkoxycarbonyl, $H_2NC(O)—$, (1-4C)alkylNHC(O)—;

and wherein at each occurrence of an R¹ substituent containing an alkyl, alkenyl, alkynyl, cycloalkyl or cycloalkenyl moiety in (R¹a), (R¹b) or (R¹c1) each such moiety is optionally further substituted on an available carbon atom with one, two, three or more substituents independently selected from F, Cl Br, OH and CN;

Q is selected from Q1 to Q6:—

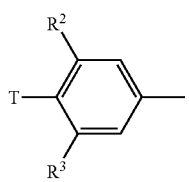

Q1

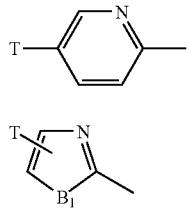

Q2

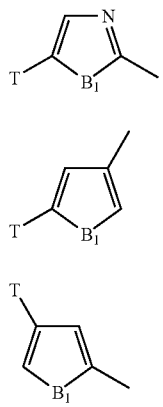

Q3

Q4

Q5

Q6

$R_2$ and $R_3$ are independently selected from H, F, Cl, $CF_3$, OMe, SMe, Me and Et;

wherein $B_1$ is O or S;

wherein T is selected from the groups in (TAa1) to (TAa12):

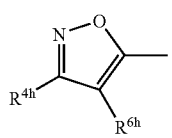

(TAa1)

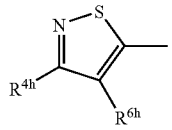

(TAa2)

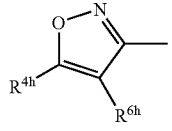

(TAa3)

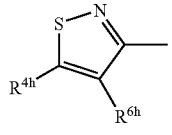

(TAa4)

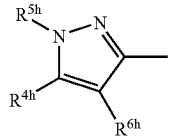

(TAa5)

-continued

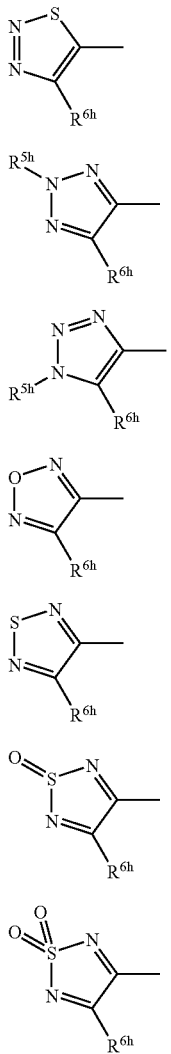

(TAa6)
(TAa7)
(TAa8)
(TAa9)
(TAa10)
(TAa11)
(TAa12)

wherein:
R$^{6h}$ is selected from hydrogen, (1-4C)alkyl, (1-4C)alkoxycarbonyl, (1-4C)alkanoyl, carbamoyl and cyano;

R$^{4h}$ and R$^{5h}$ are independently selected from hydrogen, halo, trifluoromethyl, cyano, nitro, (1-4C)alkoxy, (1-4C)alkylS(O)$_q$- (q is 0, 1 or 2), (1-4C)alkanoyl, (1-4C)alkoxycarbonyl, benzyloxy-(1-4C)alkyl, (2-4C)alkanoylamino, —CONTRcRv and —NRcRv wherein any (1-4C)alkyl group contained in the preceding values for R$^{4h}$ and R$^{5h}$ is optionally substituted by up to three substituents independently selected from hydroxy (not on C1 of an alkoxy group, and excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$- (q is 0, 1 or 2), (1-4C)alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;

R$^{4h}$ and R$^{5h}$ may further be independently selected from (1-4C)alkyl {optionally substituted by one, two or three substituents independently selected from hydroxy (excluding geminal disubstitution), oxo, trifluoromethyl, cyano, nitro, (1-4C)alkoxy, (2-4C)alkanoyloxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], hydroxyimino, (1-4C)alkoxyimino, (1-4C)alkylS(O)$_q$- (q is 0, 1 or 2), (1-4C)alkylSO$_2$—NRv-, (1-4C)alkoxycarbonyl, —CONRcRv, —NRcRv (excluding geminal disubstitution), ORc, and phenyl (optionally substituted by one, two or three substituents independently selected from (1-4C)alkyl, (1-4C)alkoxy and halo)}; wherein Rv is hydrogen or (1-4C)alkyl and Rc is as hereinafter defined; and wherein any (1-4C)alkyl group contained in the immediately preceding optional substituents (when R$^{4h}$ and R$^{5h}$ are independently (1-4C)alkyl) is itself optionally substituted by up to three substituents independently selected from hydroxy (not on C1 of an alkoxy group, and excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$- (q is 0, 1 or 2), (1-4C)alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;

or R$^{4h}$ is selected from one of the groups in (TAaa) to (TAab) below, or (where appropriate) one of R$^{4h}$ and R$^{5h}$ is selected from the above list of R$^{4h}$ and R$^{5h}$ values, and the other is selected from one of the groups in (TAaa) to (TAab) below:—

(TAaa) a group of the formula (TAaa1)

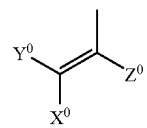

(TAaa1)

wherein Z$^0$ is hydrogen or (1-4C)alkyl;
X$^0$ and Y$^0$ are independently selected from hydrogen, (1-4C)alkyl, (1-4C)alkoxycarbonyl, halo, cyano, nitro, (1-4C)alkylS(O)$_q$- (q is 0, 1 or 2), RvRwNSO$_2$-, trifluoromethyl, pentafluoroethyl, (1-4C)alkanoyl and —CONRvRw [wherein Rv is hydrogen or (1-4C)alkyl;
Rw is hydrogen or (1-4C)alkyl];

(TAab) an acetylene of the formula -≡-H or -≡-(1-4C)alkyl;

wherein Rc is selected from groups (Rc1) to (Rc2):—
(Rc1) (1-6C)alkyl {optionally substituted by one or more (1-4C)alkanoyl groups (including geminal disubstitution) and/or optionally monosubstituted by cyano, (1-4C)alkoxy, trifluoromethyl, (1-4C)alkoxycarbonyl, phenyl (optionally substituted as for AR1 defined hereinafter), (1-4C)alkylS(O)$_q$- (q is 0, 1 or 2); or, on any but the first carbon atom of the (1-6C)alkyl chain, optionally substituted by one or more groups (including geminal disubstitution) each independently selected from hydroxy and fluoro, and/or optionally monosubstituted by oxo, —NRvRw [wherein Rv is hydrogen or (1-4C)alkyl; Rw is hydrogen or (1-4C)alkyl], (1-6C)alkanoylamino, (1-4C)alkoxycarbonylamino, N-(1-4C)alkyl-N-(1-6C)alkanoylamino, (1-4C)alkylS(O)$_p$NH— or (1-4C)alkylS(O)$_p$-((1-4C)alkyl)N— (p is 1 or 2)};

(Rc2) R$^{13}$CO—, R$^{13}$SO$_2$— or R$^{13}$CS— wherein R$^{13}$ is selected from (Rc2a) to (Rc2d):—

(Rc2a) hydrogen, (1-4C)alkoxycarbonyl, trifluoromethyl and —NRvRw [wherein Rv is hydrogen or (1-4C)alkyl; Rw is hydrogen or (1-4C)alkyl];

(Rc2b) (1-10C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkanoyl, carboxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from phosphonate [phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$- [the (1-4C)alkyl group of (1-4C)alkylS(O)$_q$- being optionally substituted by one substituent selected from hydroxy, (1-4C)alkoxy, (1-4C)alkanoyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], amino, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, carboxy, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$-((1-4C)alkyl)N—, and (1-4C)alkylS(O)$_q$-]};

(Rc2c) R$^{14}$C(O)O(1-6C)alkyl wherein R$^{14}$ is AR1, AR2, (1-4C)alkylamino (the (1-4C)alkyl group being optionally substituted by (1-4C)alkoxycarbonyl or by carboxy), benzyloxy-(1-4C)alkyl or (1-10C)alkyl {optionally substituted as defined for (Rc2b)};

(Rc2d) R$^{15}$O— wherein R$^{15}$ is benzyl, (1-6C)alkyl {optionally substituted as defined for (Rc2c)}, or AR2b;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom.

It will be noted that in the groups (Ia) to (If) there is no substituent in the position adjacent to the nitrogen link.

In this specification, where it is stated that a ring may be linked via an sp$^2$ carbon atom it is to be understood that the ring is linked via one of the carbon atoms in a C=C double bond.

In this specification the term 'alkyl' includes straight chained and branched structures. For example, (1-6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1-4C)alkyl includes 1-bromoethyl and 2-bromoethyl.

There follow particular and suitable values for certain substituents and groups which may be referred to in this specification. These values may be used where appropriate with any of the values, aspects, claims, definitions and embodiments disclosed hereinbefore, or hereinafter.

Examples of (1-4C)alkyl and (1-5C)alkyl include methyl, ethyl, propyl, isopropyl and t-butyl; examples of (1-6C)alkyl include methyl, ethyl, propyl, isopropyl, t-butyl, pentyl and hexyl; examples of (1-10C)alkyl include methyl, ethyl, propyl, isopropyl, pentyl, hexyl, heptyl, octyl and nonyl; examples of (1-4C)alkanoylamino-(1-4C)alkyl include formamidomethyl, acetamidomethyl and acetamidoethyl; examples of hydroxy(1-4C)alkyl and hydroxy(1-6C)alkyl include hydroxymethyl, 1-hydroxyethyl, 2-hydroxyethyl and 3-hydroxypropyl; examples of (1-4C)alkoxycarbonyl include methoxycarbonyl, ethoxycarbonyl and propoxycarbonyl; examples of 2-((1-4C)alkoxycarbonyl)ethenyl include 2-(methoxycarbonyl)ethenyl and 2-(ethoxycarbonyl)ethenyl; examples of 2-cyano-2-((1-4C)alkyl)ethenyl include 2-cyano-2-methylethenyl and 2-cyano-2-ethylethenyl; examples of 2-nitro-2-((1-4C)alkyl)ethenyl include 2-nitro-2-methylethenyl and 2-nitro-2-ethylethenyl; examples of 2-((1-4C)alkylaminocarbonyl)ethenyl include 2-(methylaminocarbonyl)ethenyl and 2-(ethylaminocarbonyl)ethenyl; examples of (2-4C)alkenyl include allyl and vinyl; examples of (2-4C)alkenyloxy include allyloxy and vinyloxy; examples of (2-4C)alkenylamino include allylamino and vinylamino; examples of (2-4C)alkynyl include ethynyl and 2-propynyl; examples of (1-4C)alkanoyl include formyl, acetyl and propionyl; examples of (1-4C)alkoxy include methoxy, ethoxy and propoxy; examples of (1-6C)alkoxy and (1-10C)alkoxy include methoxy, ethoxy, propoxy and pentoxy; examples of (1-4C)alkylthio include methylthio and ethylthio; examples of (1-4C)alkylamino include methylamino, ethylamino and propylamino; examples of di-((1-4C)alkyl)amino include dimethylamino, N-ethyl-N-methylamino, diethylamino, N-methyl-N-propylamino and dipropylamino; examples of halo groups include fluoro, chloro and bromo; examples of (1-4C)alkylsulfonyl include methylsulfonyl and ethylsulfonyl; examples of (1-4C)alkoxy-(1-4C)alkoxy and (1-6C)alkoxy-(1-6C)alkoxy include methoxymethoxy, 2-methoxyethoxy, 2-ethoxyethoxy and 3-methoxypropoxy; examples of (1-4C)alkoxy-(1-4C)alkoxy-(1-4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy;

examples of (1-4C)alkoxy-(1-4C)alkoxycarbonyl include methoxymethoxycarbonyl, 2-methoxyethoxycarbonyl, 2-ethoxyethoxycarbonyl and 3-methoxypropoxycarbonyl; examples of (1-4C)alkoxy-(1-4C)alkoxy-(1-4C)alkoxycarbonyl include 2-(methoxymethoxy)ethoxycarbonyl, 2-(2-methoxyethoxy)ethoxycarbonyl, 3-(2-methoxyethoxy)propoxycarbonyl and 2-(2-ethoxyethoxy)ethoxycarbonyl; examples of (1-4C)alkylS(O)$_2$amino include methylsulfonylamino and ethylsulfonylamino; examples of (1-4C)alkanoylamino, (1-4C)alkylcarbonylamino and (1-6C)alkanoylamino include formamido, acetamido and propionylamino; examples of (2-4C)alkanoylamino include acetamido and propionylamino; examples of (1-4C)alkoxycarbonylamino include methoxycarbonylamino and ethoxycarbonylamino; examples of N-(1-4C)alkyl-N-(1-6C)alkanoylamino include N-methylacetamido, N-ethylacetamido and N-methylpropionamido; examples of (1-4C)alkylS(O)$_p$NH— wherein p is 1 or 2 include methylsulfinylamino, methylsulfonylamino, ethylsulfinylamino and ethylsulfonylamino; examples of (1-4C)alkylS(O)$_p$((1-4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1-4C)alkylS(O)$_p$NH— wherein p is 1 or 2 include trifluoromethylsulfinylamino and trifluoromethylsulfonylamino; examples of fluoro(1-4C)alkylS(O)$_p$((1-4C)alkyl)NH— wherein p is 1 or 2 include trifluoromethylsulfinylmethyl amino and trifluoromethylsulfonylmethyl amino examples of (1-4C)alkoxy(hydroxy)phosphoryl include methoxy(hydroxy)phosphoryl and ethoxy(hydroxy)phosphoryl; examples of di-(1-4C)alkoxyphosphoryl include dimethoxyphosphoryl, di-ethoxyphosphoryl and ethoxy(methoxy)phosphoryl; examples of (1-4C)alkylS(O)$_q$- wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$- wherein q is 0, 1 or 2 are phenylthio, phenylsulfinyl, phenylsulfonyl and naphthylthio, naphthylsulfinyl and naphthylsulfonyl respectively; examples of benzyloxy-(1-4C)alkyl include benzyloxymethyl and benzyloxyethyl; examples of a (3-4C)alkylene chain are trimethylene or tetramethylene; examples of (1-6C)alkoxy-(1-6C)alkyl include methoxymethyl, ethoxymethyl and 2-methoxyethyl; examples of hydroxy-(2-6C)alkoxy include 2-hydroxyethoxy and 3-hydroxypropoxy; examples of (1-4C)alkylamino-(2-6C)alkoxy include 2-methylaminoethoxy and 2-ethylaminoethoxy; examples of di-(1-4C)alkylamino-(2-6C)alkoxy include 2-dimethylaminoethoxy and 2-diethylaminoethoxy; examples of phenyl(1-4C)alkyl include benzyl and phenethyl; examples of (1-4C)alkylcarbamoyl include methylcarbamoyl and ethylcarbamoyl; examples of di((1-4C)alkyl)carbamoyl include di(methyl)carbamoyl and di(ethyl)carbamoyl; examples of hydroxyimino(1-4C)alkyl include hydroxyiminomethyl, 2-(hydroxyimino)ethyl and 1-(hydroxyimino)ethyl; examples of (1-4C)alkoxyimino-(1-4C)alkyl include methoxyiminomethyl, ethoxyiminomethyl, 1-(methoxyimino) ethyl and 2-(methoxyimino)ethyl; examples of (1-4C)alkoxyimino include methoxyimino and ethoxyiminol; examples of halo(1-4C)alkyl include, halomethyl, 1-haloethyl, 2-haloethyl, and 3-halopropyl; examples of nitro(1-4C)alkyl include nitromethyl, 1-nitroethyl, 2-nitroethyl and 3-nitropropyl; examples of amino(1-4C)alkyl include aminomethyl, 1-aminoethyl, 2-aminoethyl and 3-aminopropyl; examples of cyano(1-4C)alkyl include cyanomethyl, 1-cyanoethyl, 2-cyanoethyl and 3-cyanopropyl; examples of (1-4C)alkanesulfonamido include methanesulfonamido and ethanesulfonamido; examples of (1-4C)alkylaminosulfonyl include methylaminosulfonyl and ethylaminosulfonyl; and examples of di-(1-4C)alkylaminosulfonyl include dimethylaminosulfonyl, diethylaminosulfonyl and N-methyl-N-ethylaminosulfonyl; examples of (1-4C)alkanesulfonyloxy include methylsulfonyloxy, ethylsulfonyloxy and propylsulfonyloxy; examples of (1-4C)alkanoyloxy include formyloxy, acetoxy, propanoyloxy and butanoyloxy; examples of (2-4C)alkanoyloxy include acetoxy, propanoyloxy and butanoyloxy; examples of (1-4C)alkylaminocarbonyl include methylaminocarbonyl and ethylaminocarbonyl; examples of di((1-4C)alkyl)aminocarbonyl include dimethylaminocarbonyl and diethylaminocarbonyl; examples of (3-6C)cycloalkyl and (3-8C)cycloalkyl include cyclopropyl, cyclobutyl, cyclopentyl and cyclohexyl; examples of (3-6C) cycloalkenyl include cyclopropenyl, cyclobutenyl, cyclopentenyl and cyclohexenyl; examples of (4-7C)cycloalkyl include cyclobutyl, cyclopentyl and cyclohexyl; examples of di(N-(1-4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Where optional substituents are listed such substitution is preferably not geminal disubstitution unless stated otherwise. If not stated elsewhere, suitable optional substituents for a particular group are those as stated for similar groups herein.

Preferable optional substituents on Ar2b as 1,3-dioxolanyl, 1,3-dioxan-4-yl, 1,3-dioxan-5-yl or 1,4-dioxan-2-yl are mono- or disubstitution by substituents independently selected from (1-4C)alkyl (including geminal disubstitution), (1-4C)alkoxy, (1-4C)alkylthio, acetamido, (1-4C)alkanoyl, cyano, trifluoromethyl and phenyl].

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Suitable pro-drugs for triazole derivatives include triazoliumsalts eg halides; for example a pro-drug such as:

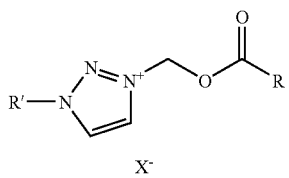

(Ref: T. Yamazaki et al. 42$^{nd}$ Interscience Conference on Antimicrobial Agents and Chemotherapy, San Diego, 2002; Abstract F820).

Suitable pro-drugs of hydroxy groups are glycosides, for example α- or β-glucosides, in the D- or L- configuration.

Further suitable pro-drugs of hydroxyl groups are acyl esters of acetal-carbonate esters of formula RCOOC(R,R') OCO—, where R is (1-4C)alkyl and R' is (1-4C)alkyl or H. Further suitable prodrugs are carbonate and carbamate esters RCOO— and RNHCOO—.

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol.

Suitable pharmaceutically-acceptable esters for carboxy include (1-6C)alkoxymethyl esters for example methoxymethyl, (1-6C)alkanoyloxymethyl esters for example pivaloyloxymethyl, phthalidyl esters, (3-8C)cycloalkoxycarbonyloxy(1-6C)alkyl esters for example 1-cyclohexylcarbonyloxyethyl; 1,3-dioxolan-2-onylmethyl esters for example 5-methyl-1,3-dioxolan-2-ylmethyl; and (1-6C)alkoxycarbonyloxyethyl esters for example 1-methoxycarbonyloxyethyl and may be formed at any carboxy group in the compounds of this invention.

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1-10C)alkanoyl, benzoyl, phenylacetyl and substituted benzoyl and phenylacetyl, (1-10C)alkoxycarbonyl (to give alkyl carbonate esters), di-(1-4C)alkylcarbamoyl and N-(di-(1-4C)alkylaminoethyl)-N-(1-4C)alkylcarbamoyl (to give carbamates), di-(1-4C)alkylaminoacetyl, carboxy(2-5C)alkylcarbonyl and carboxyacetyl. Examples of ring substituents on phenylacetyl and benzoyl include chloromethyl or aminomethyl, (1-4C)alkylaminomethyl and di-((1-4C) alkyl)aminomethyl, and morpholino or piperazino linked from a ring nitrogen atom via a methylene linking group to the 3- or 4-position of the benzoyl ring. Other interesting in-vivo hydrolysable esters include, for example, R$^4$C(O)O (1-6C)alkyl-CO— (wherein R$^4$ is for example, optionally substituted benzyloxy-(1-4C)alkyl, or optionally substituted phenyl; suitable substituents on a phenyl group in such esters include, for example, 4-(1-4C)piperazino-(1-4C) alkyl, piperazino-(1-4C)alkyl and morpholino-(1-4C)alkyl.

Further suitable in-vivo hydrolysable esters are those formed from amino acids. For examples, esters formed by reaction of a hydroxy group of a compound with the carboxylic acid of an amino acid. By the term "amino acid" herein we mean any α- or other amino substituted acid, naturally occurring or otherwise ie. non-naturally occurring, and derivatives thereof such as those formed by substitution (for example by alkylation on the nitrogen of the amino group). The use of either a natural or a non-natural amino acid represent particular and independent aspects of the invention. Examples of suitable α-amino acids and derivatives thereof, are valine, leucine, iso-leucine, N-methyl isoleucine, N-tert-butyl-isoleucine, lysine, glycine, N-methylglycine, N,N-dimethyl glycine, alanine, gluamine, asparagine, proline, and phenylalanine. In one embodiment, preferred amino acids are naturally occurring α-amino acids and N-alkylated derivatives thereof.

The use of amino acids having neutral and/or basic side chains represent particular and independent aspects of the invention.

Further suitable in-vivo hydrolysable esters of a compound of the formula (I) are described as follows. For example, a 1,2-diol may be cyclised to form a cyclic ester of formula (PD1) or a pyrophosphate of formula (PD2), and a 1,3-diol may be cyclised to form a cyclic ester of the formula (PD3):

(PD1)

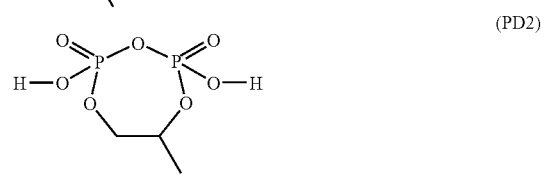

(PD2)

-continued

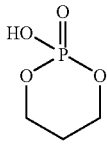
(PD3)

Esters of compounds of formula (I) wherein the HO— function/s in (PD1), (PD2) and (PD3) are protected by (1-4C)alkyl, phenyl or benzyl are useful intermediates for the preparation of such pro-drugs.

Further in-vivo hydrolysable esters include phosphoramidic esters, and also compounds of invention in which any free hydroxy group independently forms a phosphoryl (npd is 1) or phosphiryl (npd is 0) ester of the formula (PD4):

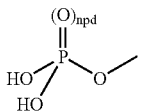
(PD4)

For the avoidance of doubt, phosphono is $-P(O)(OH)_2$; (1-4C)alkoxy(hydroxy)-phosphoryl is a mono-(1-4C)alkoxy derivative of $-O-P(O)(OH)_2$; and di-(1-4C)alkoxyphosphoryl is a di-(1-4C)alkoxy derivative of $-O-P(O)(OH)_2$.

Useful intermediates for the preparation of such esters include compounds containing a group/s of formula (PD4) in which either or both of the —OH groups in (PD4) is independently protected by (1-4C)alkyl (such compounds also being interesting compounds in their own right), phenyl or phenyl-(1-4C)alkyl (such phenyl groups being optionally substituted by 1 or 2 groups independently selected from (1-4C)alkyl, nitro, halo and (1-4C)alkoxy).

Thus, prodrugs containing groups such as (PD1), (PD2), (PD3) and (PD4) may be prepared by reaction of a compound of invention containing suitable hydroxy group/s with a suitably protected phosphorylating agent (for example, containing a chloro or dialkylamino leaving group), followed by oxidation (if necessary) and deprotection.

Other suitable prodrugs include phosphonooxymethyl ethers and their salts, for example a prodrug of R—OH such as:

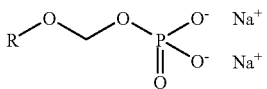

When a compound of invention contains a number of free hydroxy groups, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2), (PD3) and/or (PD4) may ionise (partially or fully) to form salts with an appropriate number of counter-ions. Thus, by way of example, if an in-vivo hydrolysable ester prodrug of a compound of invention contains two (PD4) groups, there are four HO—P— functionalities present in the overall molecule, each of which may form an appropriate salt (i.e. the overall molecule may form, for example, a mono-, di-, tri- or tetra-sodium salt).

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1-6C)alkyl-CO-$ (wherein $R^{14}$ is for example, benzyloxy-(1-4C)alkyl, or phenyl). Suitable substituents on a phenyl group in such esters include, for example, 4-(1-4C)piperazino-(1-4C)alkyl, piperazino-(1-4C)alkyl and morpholino-(1-4C)alkyl.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

In one aspect, suitable pro-drugs of the invention are in-vivo hydrolysable esters such as (1-4C)alkyl esters; (1-4C)alkyl esters substituted with (1-4C)alkoxy, (1-4C)alkoxy(1-4C)alkoxy, carboxy, (1-4C)alkyl esters, amino, (1-4C)alkylamino, di(1-4C)alkylamino, tri(1-4C)alkylamino (thereby containing a quaternised nitrogen atom), aminocarbonyl, carbamates, amides or heterocyclyl groups (for example, an ester formed by reaction of a hydroxy group in a compound of formula (I) with methoxy acetic acid, methoxypropionic acid, adipic acid momethylester, 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine, nicotinic acid, nicotinic acid —N-oxide, pyrimidine-carboxylic acid (for example pyrimidine-5-carboxylic acid), pyrazine-carboxylic acid (for example pyrazine-2-carboxylic acid), or piperidine-4-carboxylic acid); (3-6C) cycloalkyl esters (optionally substituted by a (1-4C)alkoxycarbonyl, alkoxy or carboxy group); carbonates (for example (1-4C)alkylcarbonates and such carbonates substituted by (1-4C)alkoxy or di(1-4C)alkyl)amino); sulfates; phosphates and phosphate esters; and carbamates; and pharmaceutically acceptable salts thereof.

Further suitable pro-drugs are those formed by reaction of a hydroxy group in a compound of formula (I) with carbonates, particularly alkoxysubstituted alkyl carbonates such as methoxypropylcarbonate.

Further suitable pro-drugs are esters formed by reaction of a hydroxy group in a compound of formula (I) with methoxy acetic acid, methoxypropionic acid, adipic acid momethylester, 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine, nicotinic acid, nicotinic acid —N-oxide, pyrimidine-5-carboxylic acid, pyrazine-2-carboxylic acid, or piperidine-4-carboxylic acid, 2-carboxy-cyclohexane-1-carboxylic acid; and pharmaceutically acceptable salts thereof.

Particular compounds of the invention are in-vivo hydrolysable esters formed from amino acids, and pharmaceutically acceptable salts thereof.

Further particular compounds of the invention are in-vivo hydrolysable esters formed from 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine; and pharmaceutically acceptable salts thereof.

The compounds of the present invention have a chiral centre at the C-5 position of the oxazolidinone ring. The pharmaceutically active enantiomer is of the formula (IA):

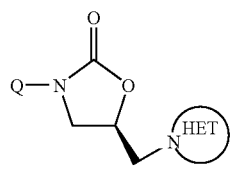

(IA)

The present invention includes the pure enantiomer depicted above or mixtures of the 5(R) and 5(S) enantiomers, for example a racemic mixture. If a mixture of enantiomers is used, a larger amount (depending upon the ratio of the enantiomers) will be required to achieve the same effect as the same weight of the pharmaceutically active enantiomer. The enantiomer depicted above may be the 5(R) or 5(S) enantiomer depending on the nature of the N—HET group (for example, when —N—HET is imidazole it is the 5(S) enantiomer).

Furthermore, some compounds of the formula (I) may have other chiral centres, for example, certain sulfoxide compounds may be chiral at the sulfur atom. It is to be understood that the invention encompasses all such optical and diastereo-isomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

Furthermore, some compounds of the formula (I), for example certain sulfoxide compounds may exist as cis- and trans- isomers. It is to be understood that the invention encompasses all such isomers, and mixtures thereof, that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens, including organisms known to be resistant to most commonly used antibiotics. They have good physical and/or pharmacokinetic properties in general, and favourable toxicological and MAO profiles.

Particularly preferred compounds of the invention comprise a compound of formula (I), or a pharmaceutically-acceptable salt or an in-vivo hydrolysable ester thereof, wherein the substituents Q, —N—HET (which may also be described as HET herein), T and other substituents mentioned above have values disclosed hereinbefore, or any of the following values (which may be used where appropriate with any of the definitions and embodiments disclosed hereinbefore or hereinafter):

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of the formula (I).

Preferably Q is selected from Q1, Q2, Q4 and Q6; especially Q1 and Q2; and most preferably Q is Q1.

In one embodiment $R^1$ is (1-4C)alkyl. Preferably $R^1$ is methyl.

In one embodiment $R^1$ has values ($R^1$a) to ($R^1$c1).

Preferable $R^1$ groups are those of (R1a) and ($R^1$b).

In ($R^1$b) the substituted (1-4C)alkyl group is preferably a substituted methyl group.

Preferable ($R^1$) groups provided by optional F and/or Cl and/or one cyano further substituents in ($R^1$a) and ($R^1$b) are, for example, $R^1$ as trifluoromethyl, —CHF$_2$, —CH$_2$F, —CH$_2$CN, —CF$_2$NH(1-4C)alkyl, —CF$_2$CH$_2$OH, —CH$_2$OCF$_3$, —CH$_2$OCHF$_2$, —CH$_2$OCH$_2$F, —NHCF$_2$CH$_3$.

Suitable values for $R^1$c1 are azetidinyl, (N- or C-linked), oxetanyl and thietanyl.

In one aspect $R^1$ is preferably selected from a substituent from the groups $R^1$a, $R^1$b and $R^1$d wherein:

($R^1$a) halogen, hydroxy, (1-4C)alkoxy, (2-4C)alkenyloxy, (2-4C)alkenyl, (2-4C)alkynyl (optionally substituted on the terminal carbon by CH$_2$=CH—, di(1-4C)alkylamino, AR2, AR2a or AR2b), (3-6C)cycloalkyl, (3-6C)cycloalkenyl, (1-4C)alkyl-S(O)q- (wherein q is 0), amino, (1-4C)alkylcarbonylamino, (1-4C)alkylamino, di-(1-4C)alkylamino and (2-4C)alkenylamino;

($R^1$b) a (1-4C)alkyl group which is substituted by one substituent selected from hydroxy, halo, (1-4C)alkoxy, amino, (1-4C)alkylamino, di-(1-4C)alkylamino, (1-4C)alkyl-S(O)q- (wherein q is 0, 1 or 2), cyano and azido, (3-6C)cycloalkyl, AR1-S(O)q- (wherein q is 0, 1 or 2 and AR1 is defined hereinbelow), AR2-S(O)q- (wherein q is 0, 1 or 2), AR2a-S(O)q- (wherein q is 0, 1 or 2), benzyl-S(O)q- (wherein q is 0, 1 or 2), (1-4C)alkyl-OCO—NH—, (1-4C)alkyl-N-HCO—O—, (1-4C)alkylaminocarbonyl, di(1-4C)alkylaminocarbonyl and H$_2$NC(=NH)S—;

($R^1$d) cyano, nitro, azido, formyl, (1-4C)alkylcarbonyl, (1-4C)alkoxycarbonyl, H$_2$NC(O)—, ((1-4C)alkyl)NHC(O)—;

and wherein at each occurrence of an $R^1$ substituent containing an alkyl, alkenyl, alkynyl, cycloalkyl or cycloalkenyl moiety in ($R^1$a) or ($R^1$b) each such moiety is optionally further substituted on an available carbon atom with one, two, three or more substituents independently selected from F, Cl, Br, OH and CN.

In another aspect $R^1$ is preferably selected from a substituent from the groups $R^1a$, $R^1b$ and $R^1d$, wherein:

($R^1a$) halogen, hydroxy, (1-4C)alkoxy, (2-4C)alkenyl, (2-4C)alkynyl, -ethynyl-ethene, -ethynyl-AR2, -ethynyl-AR2a, -but-2-ynyl-4-AR2a, -but-2-ynyl-4-AR2b, -but-2-ynyl-4-di-(1-4C)alkylamino, (3-6C)cycloalkyl, (1-4C)alkyl-S(O)q- (wherein q is 0), (1-4C)alkylcarbonylamino and amino, ($R^1b$) a (1-4C)alkyl group which is substituted by one substituent selected from hydroxy, halo, (1-4C)alkoxy, amino, di(1-4C)alkylamino, cyano, azido, (1-4C)alkyl-S(O)q- (wherein q is 0, 1 or 2), AR2-S(O)q- (wherein q is 0), benzyl-S(O)q- (wherein q is 0), (1-4C)alkyl-OCO—NH—, (1-4C)alkyl-NHCO—O—, di(1-4C)alkylaminocarbonyl and $H_2NC(=NH)S$—;

($R^1d$) cyano, nitro, formyl, (1-4C)alkoxycarbonyl and $H_2NC(O)$—;

and wherein at each occurrence of an $R^1$ substituent containing an alkyl, alkenyl, alkynyl, cycloalkyl or cycloalkenyl moiety in ($R^1a$) or ($R^1b$) each such moiety is optionally further substituted on an available carbon atom with one, two or three substituents independently selected from F, Cl, Br, OH and CN.

When $R^1a$ is -ethynyl-AR2, conveniently AR2 is a 5-membered ring, particularly AR2 is oxazolyl, isoxazolyl, thiazolyl or thiadiazolyl.

When $R^1a$ is -ethynyl-AR2a or -but-2-ynyl-4-AR2a, conveniently AR2a is a 5 membered ring, particularly AR2a as 3-pyrroline, 2H-pyrrole or pyrazoline.

When $R^1a$ is -but-2-ynyl-4-AR2b, conveniently AR2b a 6-membered ring such as morpholine.

In a further aspect $R^1$ is most preferably
(a) halogen, in particular fluorine, chlorine, or bromine; or
(b) cyano; or
(c) monosubstituted (1-4C)alkyl, in particular fluoromethyl, choromethyl, bromomethyl, cyanomethyl, azidomethyl, hydroxymethyl; or
(d) disubstituted (1-4C)alkyl, for example difluoromethyl, or
(e) trisubstituted (1-4C)alkyl, for example trifluoromethyl; or
(f) ethynyl or substituted ethynyl; or
(g) nitro In one embodiment T is selected from the groups of formula (TAa1) to (TAa12) defined herein. Particular values of T are groups of formula (TAa9 to TAa12).

In another embodiment T is selected from the groups of formula (TAa1) to (TAa8). Particular values of T are groups of the formula (TAa5) to (TAa8).

In a preferred embodiment, T is selected from (TAa1 to TAa4), TAa7 and TAa8. Particular values of T are groups of the formula (TAa1 to TA4).

In another embodiment, T is selected from TAa1, TAa3, TAa5, TAa7 and TAa8. Particular values for T are TAa1, TAa5, TAa7 and TAa8.

Especially preferred is each of these values of T when present in Q1 and Q2, particularly in Q1.

Preferably $R^{6h}$ is hydrogen or (1-4C)alkyl, more preferably $R^{6h}$ is hydrogen.

In one embodiment $R^{4h}$ and $R^{5h}$ are independently selected from hydrogen, halo, cyano, (1-4C)alkoxycarbonyl, (1-4C)alkanoyl, —CONRcRv {wherein Rc is hydrogen or (1-4C)alkyl; Rv is hydrogen or (1-4C)alkyl} and (1-4C)alkyl [optionally substituted with hydroxy, cyano, ORc (wherein Rc is selected from Rc1 and Rc2 as hereinbefore defined), phenyl {optionally subsituted by 1, 2 or 3 substituents independently selected from (1-4C)alkyl, (1-4C)alkoxy and halo} and (1-4C)alkoxy].

In one embodiment, $R^{4h}$ and $R^{5h}$ are independently selected from hydrogen, halo, cyano, (1-4C)alkoxycarbonyl, (1-4C)alkanoyl, —CONRcRv {wherein Rc is hydrogen or (1-4C)alkyl; Rv is hydrogen or (1-4C)alkyl} and (1-4C)alkyl [optionally substituted with hydroxy, cyano, ORc (wherein Rc is selected from Rc1 and Rc2 as hereinbefore defined), phosphoryl, phenyl {optionally substituted by 1, 2 or 3 substituents independently selected from (1-4C)alkyl, (1-4C)alkoxy and halo} and (1-4C)alkoxy];.

In another embodiment, $R^{4h}$ and $R^{5h}$ are independently selected from hydrogen, cyano, hydroxy(1-4C)alkyl, cyano (1-4C)alkyl, phosphoryl(1-4C)alkyl, benzyl (optionally substituted on the phenyl ring by one substituent selected from halo, methyl and methoxy), (1-4C)alkyl, (1-4C)alkyl substituted with ORc (wherein Rc is $R^{13}CO$ and $R^{13}$ is, selected from Rc2b), (1-4C)alkanoyl and (1-4C)alkoxycarbonyl.

In a further embodiment, $R^{4h}$ and $R^{5h}$ are independently selected from hydrogen, cyano, hydroxymethyl, cyanomethyl, phosphorylmethyl, methoxybenzyl, methyl, formyl and ethoxycarbonyl.

In a preferred embodiment, $R^{4h}$ is selected from methyl, cyano, formyl, ethoxycarbonyl, hydroxymethyl and phosphorylmethyl; and $R^{5h}$ is selected from hydrogen, methyl, methoxybenzyl and cyanomethyl. When $R^{4h}$ and $R^{5h}$ are both present (that is, in TAa5) $R^{5h}$ is preferably hydrogen or methyl.

When $R^{4h}$ and $R^{5h}$ are independently selected from optionally substituted (as defined) (1-4C)alkyl, preferably there are one or two substituents, most especially just one substituent; and when the optional substituent is —CONRcRv or —NRcRv, Rc is preferably hydrogen, (1-4C)alkyl or (1-4C)alkanoyl.

In a further preferred embodiment, $R^{4h}$ is (1-4C)alkyl substituted with hydroxy and with ORc, where Rc is selected from any of the definitions for Rc given hereinbefore or hereinafter, particularly those definitions for Rc in aspects (c) to (g) below.

The above preferred values of (TAa) are particularly preferred when present in Q1 or Q2, especially Q1. Most preferable is (TAa1) with preferable $R^{4h}$ substituents as hereinbefore defined.

Preferable values for other substituents (which may be used where appropriate with any of the definitions and embodiments disclosed hereinbefore or hereinafter) are:—
(a) —N—HET is preferably of formula (Ic), (Id) or (If).
(b) In one aspect preferably one of $R^2$ and $R^3$ is hydrogen and the other fluoro. In another aspect both $R^2$ and $R^3$ are fluoro.
(c) In one aspect Rc is $R^{13}CO$— and $R^{13}$ is selected from (1-4C)alkoxycarbonyl, hydroxy(1-4C)alkyl, (1-4C)alkyl (optionally substituted by one or two hydroxy groups, or by a (1-4C)alkanoyl group), (1-4C)alkylamino, dimethylamino(1-4C)alkyl, (1-4C)alkoxymethyl, (1-4C)alkanoylmethyl, (1-4C)alkanoyloxy(1-4C)alkyl, (1-5C)alkoxy and 2-cyanoethyl.
(d) In another aspect Rc is $R^{13}CO$— and $R^{13}$ is (1-4C)alkyl substituted with one substituent selected from (1-4C)alkoxy-(1-4C)alkoxy, (1-4C)alkoxy-(1-4C)alkoxy-(1-4C)alkoxy, phosphoryl [—O—$P(O)(OH)_2$, and mono- and di-(1-4C)alkoxy derivatives thereof], phosphiryl [—O—$P(OH)_2$ and mono- and di-(1-4C) alkoxy derivatives thereof], phosphonate [phosphono, —$P(O)(OH)_2$, and mono- and di-(1-4C)alkoxy derivatives thereof], phosphinate [—$P(OH)_2$ and mono- and di-(1-4C)alkoxy derivatives thereof], (1-4C)alkoxycarbonyl, (1-4C)alkoxy-(1-4C)alkoxycarbonyl and (1-4C)alkoxy-(1-4C)alkoxy-(1-4C)alkoxycarbonyl.

(e) In a further aspect $R^{13}$ is selected from 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy and 2-cyanoethyl.

(f) In a further aspect $R^{13}$ is selected from 1,2-dihydroxyethyl, 1,3-dihydroxyprop-2-yl and 1,2,3-trihydroxyprop-1-yl.

(g) In another aspect preferably $R^{13}$ is hydrogen, (1-10C)alkyl [optionally substituted by one or more hydroxy] or $R^{14}C(O)O(1-6C)$alkyl.

For compounds of formula (I) preferred values for Rc are those in group (Rc2) when present in any of the definitions herein containing Rc.

Where the number of optional substituents on a group is not otherwise preferably defined, the preferable number of optional substituents is one.

Especially preferred compounds of the present invention are of the formula (IB):

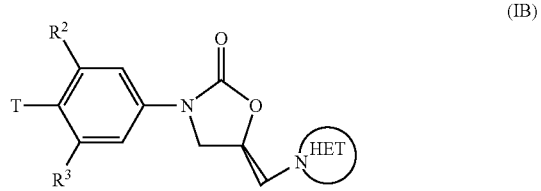

wherein —N—HET is 1,2,3-triazol-1-yl or tetrazol-2-yl;
$R^2$ and $R^3$ are independently hydrogen or fluoro; and
T is selected from (TAa1 to TAa4), TAa5, TAa7 and TAa8;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is selected from $R^1$a to $R^1$d;
$R^2$ and $R^3$ are independently hydrogen or fluoro; and
T is selected from TAa1, TAa5, TAa7 and TAa8; or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is (1-4C)alkyl;
$R^2$ and $R^3$ are independently hydrogen or fluoro; and
T is selected from TAa1, TAa5, TAa7 and TAa8; or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is selected from $R^1$a to $R^1$d;
$R^2$ and $R^3$ are independently hydrogen or fluoro;
T is selected from TAa1, TAa5, TAa7 and TAa8;
$R^{6h}$ is hydrogen or (1-4C)alkyl;
$R^{4h}$ and $R^{5h}$ are independently selected from hydrogen, cyano, hydroxy(1-4C)alkyl, cyano(1-4C)alkyl, phosphoryl(1-4C)alkyl, benzyl (optionally substituted on the phenyl ring by one substituent selected from halo, methyl and methoxy), (1-4C)alkyl, (1-4C)alkyl substituted with ORc (wherein Rc is $R^{13}$CO and $R^{13}$ is selected from Rc2b), (1-4C)alkanoyl and (1-4C)alkoxycarbonyl; or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is (1-4C)alkyl;
$R^2$ and $R^3$ are independently hydrogen or fluoro;
T is selected from TAa1, TAa5, TAa7 and TAa8;
$R^{6h}$ is hydrogen or (1-4C)alkyl;
$R^{4h}$ and $R^{5h}$ are independently selected from hydrogen, cyano, hydroxy(1-4C)alkyl, cyano(1-4C)alkyl, phosphoryl(1-4C)alkyl, benzyl (optionally substituted on the phenyl ring by one substituent selected from halo, methyl and methoxy), (1-4C)alkyl, (1-4C)alkyl substituted with ORc (wherein Rc is $R^{13}$CO and $R^{13}$ is selected from Rc2b), (1-4C)alkanoyl and (1-4C)alkoxycarbonyl;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is selected from $R^1$a to $R^1$d;
$R^2$ and $R^3$ are independently hydrogen or fluoro;
T is selected from TAa1, TAa5, TAa7 and TAa8;
$R^{4h}$ (1-4C)alkyl substituted with ORc and hydroxy;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is (1-4C)alkyl;
$R^2$ and $R^3$ are independently hydrogen or fluoro;
T is selected from TAa1, TAa5, TAa7 and TAa8;
$R^{4h}$ (1-4C)alkyl substituted with ORc and hydroxy;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is selected from $R^1$a to $R^1$d;
$R^2$ and $R^3$ are independently hydrogen or fluoro;
T is selected from TAa1, TAa5, TAa7 and TAa8;
$R^{6h}$ is hydrogen or methyl;
$R^{4h}$ is selected from methyl, cyano, formyl, ethoxycarbonyl, hydroxymethyl and phosphorylmethyl;
$R^{5h}$ is selected from hydrogen, methyl, methoxybenzyl and cyanomethyl;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;
$R^1$ is (1-4C)alkyl;
$R^2$ and $R^3$ are independently hydrogen or fluoro;
T is selected from TAa1, TAa5, TAa7 and TAa8;
$R^{6h}$ is hydrogen or methyl;
$R^{4h}$ is selected from methyl, cyano, formyl, ethoxycarbonyl, hydroxymethyl and phosphorylmethyl;
$R^{5h}$ is selected from hydrogen, methyl, methoxybenzyl and cyanomethyl;
or pharmaceutically-acceptable salts or in-vivo hydrolysable esters thereof.

Further especially preferred compounds are of the formula (IB)
wherein —N—HET is 1,2,3-triazol-1-yl or tetrazol-2-yl;

$R^1$ is selected from halogen, cyano, fluoromethyl, choromethyl, bromomethyl, cyanomethyl, azidomethyl, hydroxymethyl, difluoromethyl, trifluoromethyl, ethynyl, substituted ethynyl, and nitro;

$R^2$ and $R^3$ are independently hydrogen or fluoro;

T is selected from TAa1, TAa5, TAa7 and TAa8;

$R^{6h}$ is hydrogen or methyl;

$R^{4h}$ is selected from methyl, cyano, formyl, ethoxycarbonyl, hydroxymethyl and phosphorylmethyl;

$R^{5h}$ is selected from hydrogen, methyl, methoxybenzyl and cyanomethyl;

or pharmaceutically-acceptable salts or in-vivo hydrolysable esters thereof.

Further especially preferred compounds are of the formula (IB)

wherein —N—HET is 1,2,3-triazol-1-yl or tetrazol-2-yl;

$R^1$ is methyl;

$R^2$ and $R^3$ are independently hydrogen or fluoro;

T is selected from TAa1, TAa5, TAa7 and TAa8;

$R^{6h}$ is hydrogen or methyl;

$R^{4h}$ is selected from methyl, cyano, formyl, ethoxycarbonyl, hydroxymethyl and phosphorylmethyl;

$R^{5h}$ is selected from hydrogen, methyl, methoxybenzyl and cyanomethyl;

or pharmaceutically-acceptable salts or in-vivo hydrolysable esters thereof.

In all of the above aspects and preferred compounds of formula (IB), in-vivo hydrolysable esters are preferred where appropriate, especially phosphoryl esters (as defined by formula (PD1)–(PD4) with npd as 1).

In all of the above definitions the preferred compounds are as shown in formula (IA), i.e. the pharmaceutically active enantiomer.

Particular compounds of the present invention include each one of the Examples, in particular Example No. 1. Each one of the Examples provides a further independent aspect of the invention.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Greene and Peter Wuts (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro)phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference: WO 94-13649; WO 98-54161; WO 99-64416; WO 99-64417; WO 00-21960; WO 01-40222.

The skilled organic chemist will be able to use and adapt the information contained and referenced within the above references, and accompanying Examples therein and also the Examples herein, to obtain necessary starting materials, and products.

Thus, the present invention also provides that the compounds of the formula (I) and pharmaceutically-acceptable salts and in vivo hydrolysable esters thereof, can be prepared by a process (a) to (g) as follows (wherein the variables are as defined above unless otherwise stated):

(a) by modifying a substituent in, or introducing a new substituent into, the substituent group Q of another compound of formula (I)—for instance by (i) displacement of a functional group from a compound of formula (I) by another functional group, (ii) by oxidation or (iii) reduction of a compound of formula (I), by (iv) addition of a reagent to or (v) elimination of a reagent from a compound of formula (I), by (vi) metathesis of a compound of formula (I) into a modified compound of formula (I), or by (vii) rearrangement of a compound of formula (I) to an isomeric compound of formula (I) (Scheme I shows two examples drawn from the range of suitable methods); or (b) by reaction of a compound of formula (II):

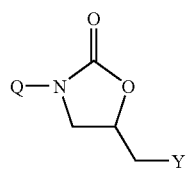

(II)

wherein Y is a displaceable group (which may be preformed, such as chloro or mesylate, or generated in-situ, for example under Mitsunobu conditions) with a compound of the formula (III):

—N—HET (III)

wherein —N—HET (of formula (Ia) to (If), already substituted and optionally protected) is HN—HET (free-base form) or ⁻N—HET anion formed from the free base form (Scheme II shows examples drawn from the range of suitable methods); or (c) by reaction of a compound of the formula (IV):

Q-Z (IV)

wherein Z is an isocyanate, amine or urethane group with an epoxide of the formula (V) wherein the epoxide group serves as a leaving group at the terminal C-atom and as a protected hydroxy group at the internal C-atom; or with a related compound of formula (VI) where the hydroxy group at the internal C-atom is conventionally protected e.g. with an acetyl group and where the leaving group Y at the terminal C-atom is a conventional leaving group e.g. a chloro- or mesyloxy-group.

(V)

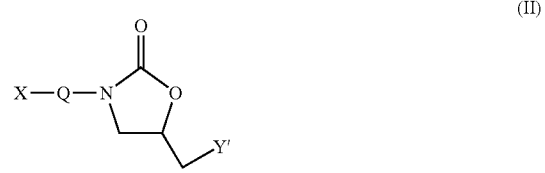

(VI)

(Scheme III shows examples drawn from the range of suitable methods), or (d) (i) by coupling, using catalysis by transition metals such as palladium(0), of a compound of formula (VII):

(II)

wherein Y' is a group —N—HET as hereinbefore defined, X is a replaceable substituent—such as chloride, bromide, iodide, or trifluoromethylsulfonyloxy; with a compound of the formula (III), or an analogue thereof, which is suitable to give a T substituent as defined by (TAa1–TAa12) in which the link is via an sp² carbon atom (D=CH=C—Lg where Lg is a leaving group such as chloride, bromide, iodide, or trifluoromethylsulfonyloxy; or as in the case of reactions carried out under Heck reaction conditions Lg may also be hydrogen)

$$T_1 \atop T_2 \diagdown D \diagup$$

(VIII)

where $T_1$ and $T_2$ may be the same or different and comprise a precursor to a ring of type T as hereinbefore defined, or $T_1$ and $T_2$ may together with D form a ring of type T as hereinbefore defined (Scheme IV shows examples drawn from the range of suitable methods);

(d) (ii) by coupling, using catalysis by transition metals such as palladium(0), of a compound of formula (VIIA):

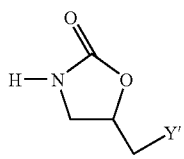
(VIIA)

wherein Y' is a group HET as hereinbefore defined, with a compound

[Aryl]-X where X is a replaceable substituent—such as chloride, bromide, iodide, or trifluoromethylsulfonyloxy, or an analogue thereof (Scheme IV shows an example drawn from the range of suitable methods);

(e) Where N—HET is 1,2,3-triazole there is the additional possibility by cycloaddition via the azide (wherein Y in (II) is azide), with a substituted acetylene or masked acetylene (such as a vinyl sulfone, a nitroloefin, or an enamine, or a substituted cyclohexa-1,4-diene derivative (Scheme II shows examples drawn from the range of suitable methods);

(f) Where N—HET is 1,2,3-triazole there is the additional possibility of synthesis with a compound of formula (IX), namely the arenesulfonylhydrazone of acetaldehyde, by reaction of a compound of formula (II) where Y=NH$_2$ (primary amine), as illustrated in Scheme V.

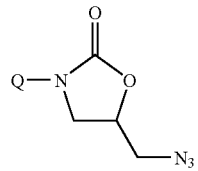
(II: Y = NH2)

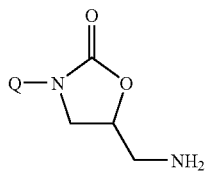
(IX)

(g) Where N—HET is 1,2,3-triazole there is the additional possibility of regioselective synthesis by cycloaddition via the azide (wherein Y in (II) is azide) with acetylene using Cu(I) catalysis in e.g. aqueous alcoholic solution at ambient temperatures to give the N-1,2,3-triazole, as illustrated in Scheme VI.

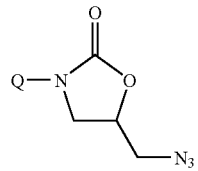
(II: Y = N$_3$)

and thereafter if necessary: (i) removing any protecting groups; (ii) forming a pharmaceutically-acceptable salt; (iii) forming an in-vivo hydrolysable ester.

The main synthetic routes are illustrated in Schemes (I) to (VI) below (with Q as phenyl, and T, R$^1$, R$^2$, and R$^3$ defined with reference to analogous substituents defined elsewhere herein). The compounds of the invention may be prepared by analogous chemistry adapted from these Schemes. Schemes (II) and (VI) also show the preparation of 1,2,3-triazoles via the azide (prepared from the relevant hydroxy compound) and the amine (prepared e.g. from the azide) respectively.

Scheme I

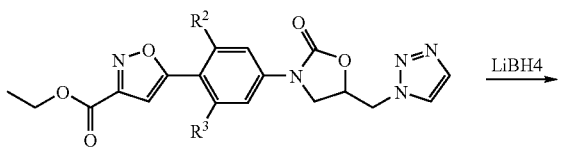

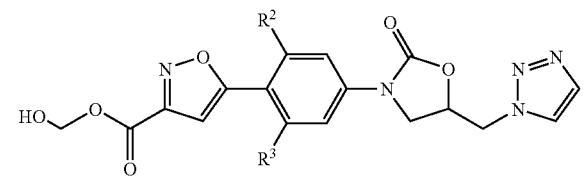

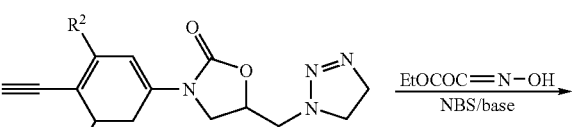

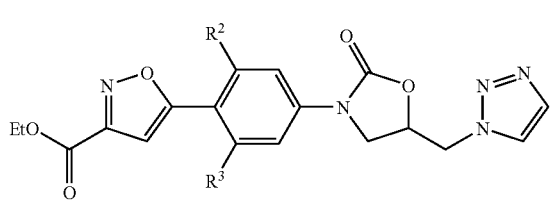

Scheme II
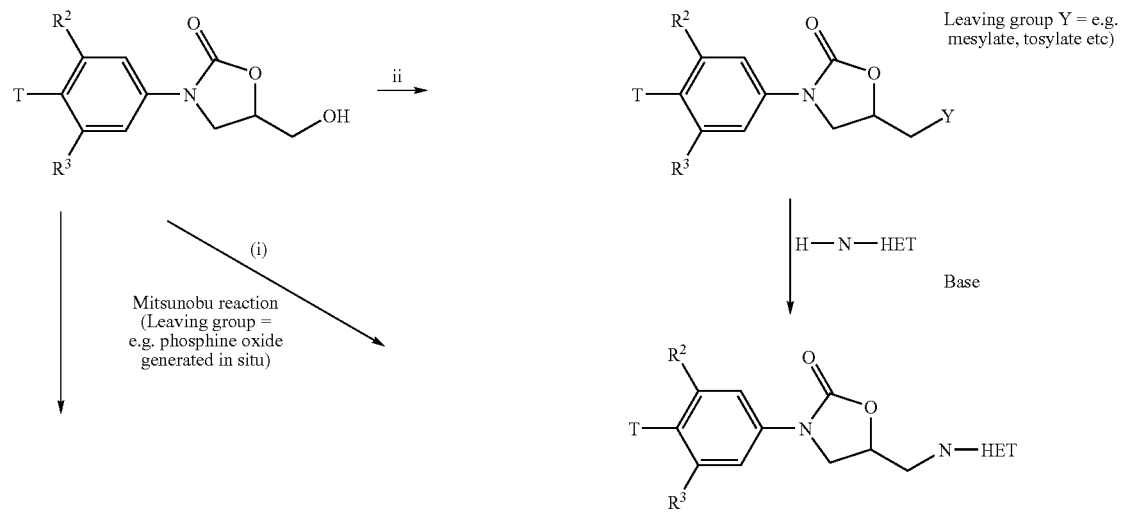
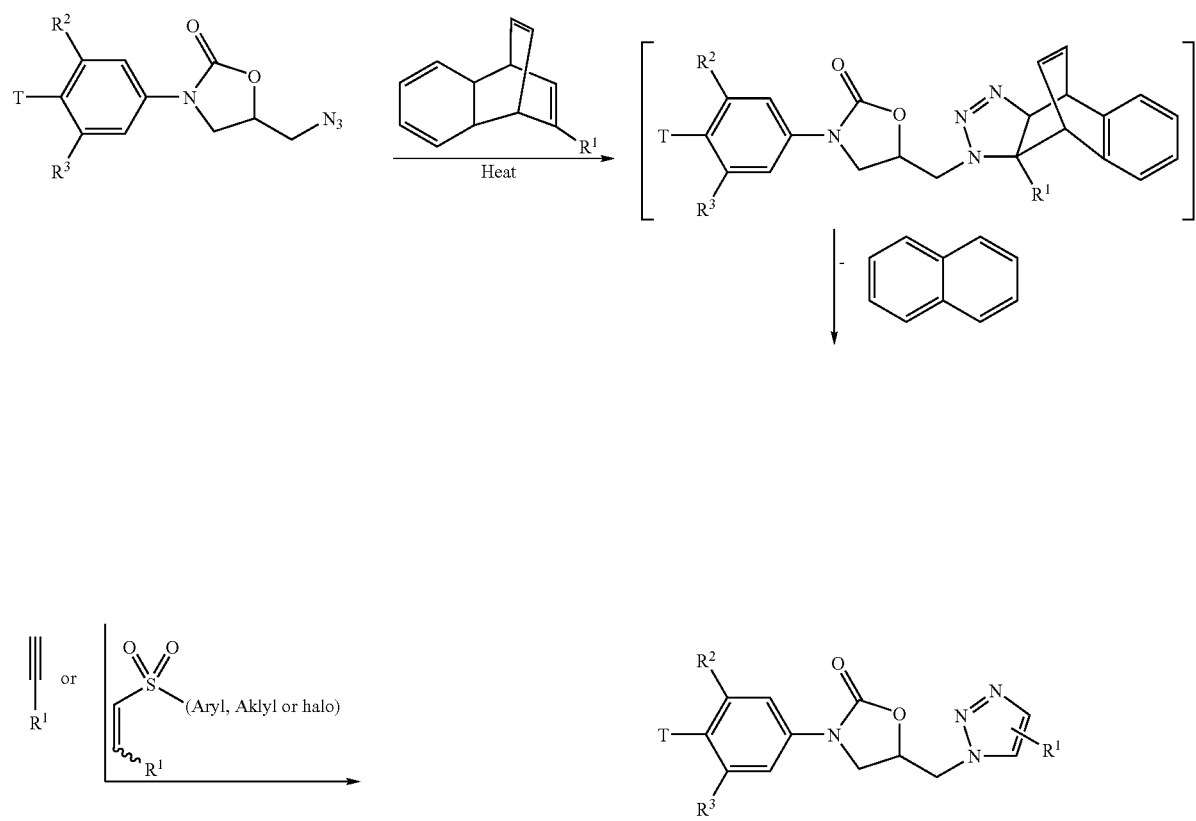

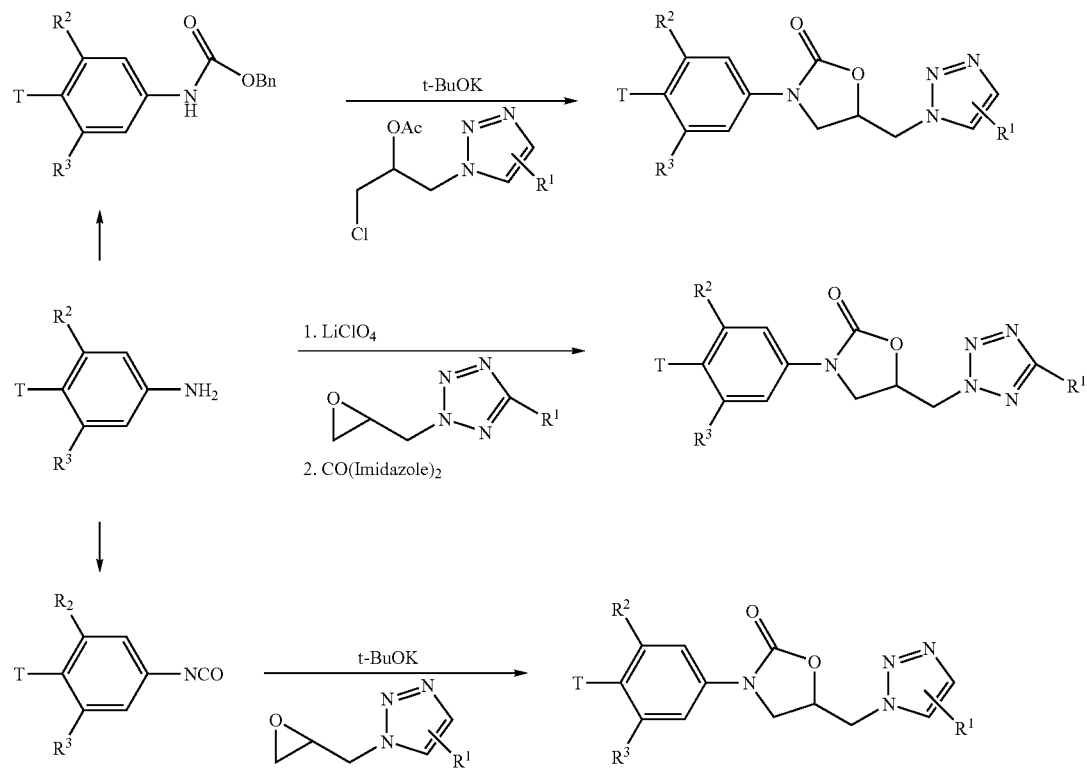
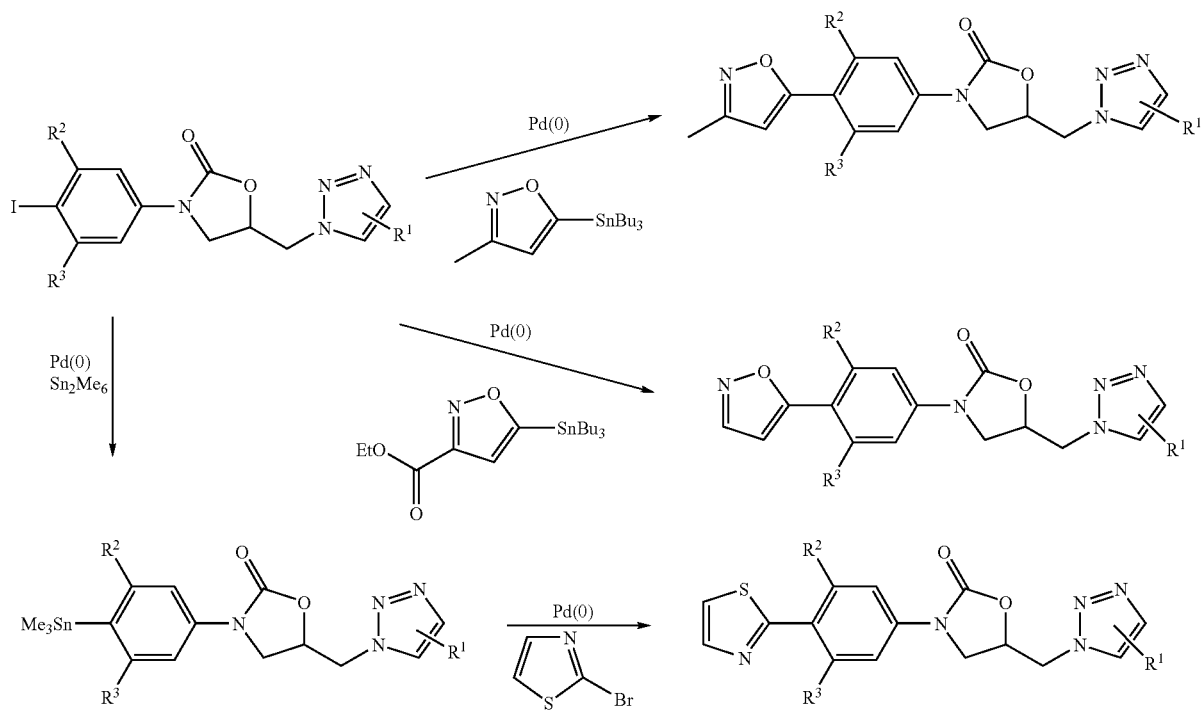

-continued

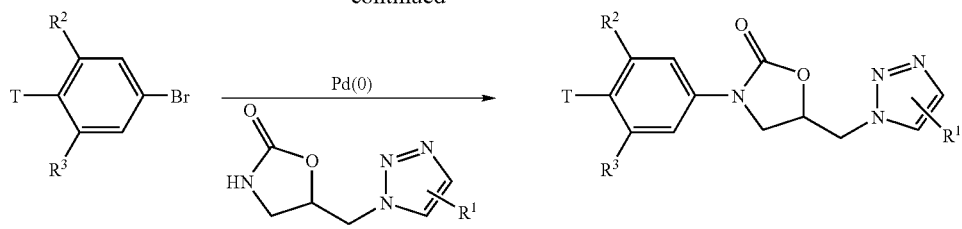

Scheme V

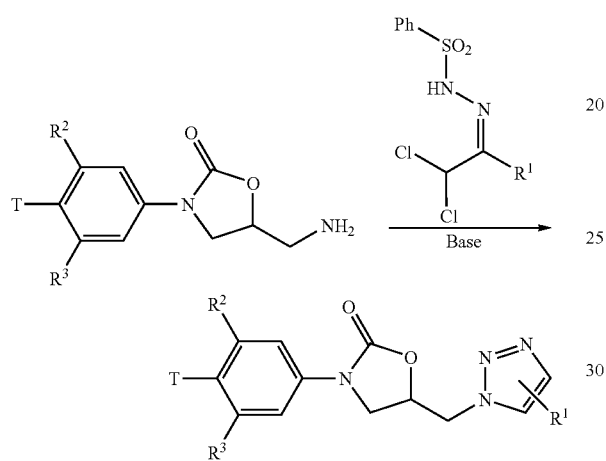

Scheme VI

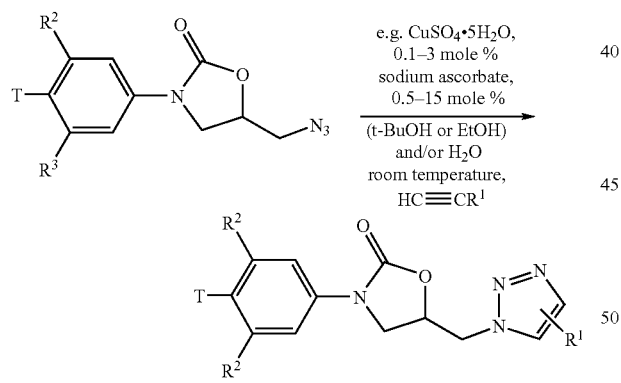

Deprotection, salt formation or in-vivo hydrolysable ester formation may each be provided as a specific final process step.

The N-linked hetereocycle can of course be prepared early in the overall synthesis, and then other functional groups changed.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J. Wiley & Sons), 1992.

Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, for example International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (1), for example, acylation of a group of formula (TC5) wherein Rc is hydrogen.

(b)(i) Reaction (b)(i) (in which Y is initially hydroxy) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Compounds of the formula (II) wherein Y is hydroxy may be obtained as described in the references cited herein (particularly in the section proceeding the discussion of protecting groups), for example, by reacting a compound of the formula (X) with a compound of formula (XI):

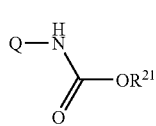

(X)

-continued

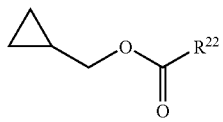

(XI)

wherein $R^{21}$ is (1-6C)alkyl or benzyl and $R^{22}$ is (1-4C)alkyl or —S(O)$_n$(1-4C)alkyl where n is 0, 1 or 2. Preferably $R^{22}$ is (1-4C)alkyl.

In particular, compounds of the formula (II), (X) and (XI) may be prepared by the skilled man, for example as described in International Patent Application Publication Nos. WO95/07271, WO97/27188, WO 97/30995, WO 98/01446 and WO 98/01447, the contents of which are hereby incorporated by reference, and by analogous processes.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt. I (1993), 45–225, B. J. Wakefield.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25–60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux When Y is (1-4C)alkanesulfonyloxy or tosylate the compound (II) may be prepared by reacting the hydroxy compound with (1-4C)alkanesulfonyl chloride or tosyl chloride in the presence of a mild base such as triethylamine or pyridine.

When Y is a phosphoryl ester (such as (PhO)$_2$—P(O)—O—) or Ph$_2$—P(O)—O— the compound (II) may be prepared from the hydroxy compound under standard conditions.

(c) Reaction (c) is performed under conditions analogous to those described in the following references which disclose how suitable and analogous starting materials may be obtained.

Reaction (c) is especially suitable for compounds in which H—N—HET is a weakly acidic heterocycle (such as, for example, triazole or tetrazole).

Compounds of the formula Q-Z wherein Z is an isocyanate may be prepared by the skilled chemist, for example by analogous processes to those described in Walter A. Gregory et al in J. Med. Chem. 1990, 33, 2569–2578 and Chung-Ho Park et al in J. Med. Chem. 1992, 35, 1156–1165. Compounds of the formula Q-Z wherein Z is a urethane may be prepared by the skilled chemist, for example by analogous processes to those described in International Patent Application Publication Nos. WO 97/30995 and WO 97/37980.

A similar reaction to reaction (c) may be performed in which Q-Z wherein Z is a amine group is reacted with the epoxide (optionally in the presence of an organic base), and the product is reacted with, for example, phosgene to form the oxazolidinone ring. Such reactions and the preparation of starting materials in within the skill of the ordinary chemist with reference to the above-cited documents disclosing analogous reactions and preparations.

Epoxides of the formula (V) may be prepared from the corresponding compound of formula (XII):

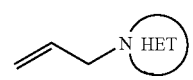

(XII)

Certain such epoxide and alkene intermediates are novel and are provided as a further feature of the invention. Asymmetric epoxidation may be used to give the desired optical isomer. Compounds of formula (VI) may be obtained from epoxides of formula (V); alternatively compounds of formula (VI) may be used as precursors for epoxides of formula (V) according to the relative ease of synthesis in each case. The skilled chemist will appreciate that the epoxides of formula (V) and the compounds of formula (VI) are structurally equivalent and the choice between them will be made on the grounds of availability, convenience, and cost.

(d) The transition metal catalysed coupling reaction to form a C—C or N—C bond from the corresponding aryl derivatives and the arenes, heteroarenes, olefins, alkynes, or amines is performed under conventional conditions (see for instance J. K. Stille, Angew. Chem. Int. Ed. Eng., 1986, 25, 509–524; N. Miyaura and A. Suzuki, Chem. Rev., 1995, 95, 22457–2483; D. Baranano, G. Mann, and J. F. Hartwig, Current Org. Che., 1997, 1, 287–305; S. P. Stanforth, Tetrahedron, 1998, 54, 263–303). The reaction d (ii) may be conveniently carried out under the conditions described in Tetrahedron Letters (2001), 42(22), 3681–3684, or in the analogous conventional conditions described in the above mentioned literature. In such a procedure a preferred variation of X may be bromine.

(e) The cycloaddition reaction to form 1,2,3 triazoles from the corresponding azide is performed under conventional conditions. Compounds of the formula (II) wherein Y is azide may be obtained as described in the references cited herein (particularly in the section proceeding the discussion of protecting groups), for example from the corresponding compounds in which Y is hydroxy or mesylate.

(f) The reaction of amines of formula (II, Y═NH2) with arenesulfonyl hydrazones to form 1,2,3 triazoles may be carried out as described in the literature (Sakai, Kunikazu; Hida, Nobuko; Kondo and Kiyosi: "Reactions of α-polyhalo ketone tosylhydrazones with sulfide ion and primary amines. Cyclization to 1,2,3-thiadiazoles and 1,2,3-triazoles." *Bull. Chem. Soc. Jpn.* (1986), 59(1), 179–83; Sakai, Kunikazu; Tsunemoto, Daiei; Kobori, Takeo; Kondo, Kiyoshi; Hida and Nobuko: 1,2,3-Trihetero 5-membered heterocyclic compounds, EP 103840 A2 19840328). The leaving groups Y', Y" may be chloro or any other group capable of being eliminated from the arenesulfonyl hydrazone during the reaction with the amine. The skilled chemist will also appreciate that a similar reaction may be used to produce other substituted triazoles suitable for incorporation into related processes such as reaction with compounds of formula (IV) in process (c).

g) The reaction of azides of formula (II, Y═$N_3$) with terminal alkynes using Cu(I) catalysis to give regioselectively 4-substituted 1,2,3-triazole compounds of formula (I) may be carried out as described in the literature (for instance V. V. Rostovtsev, L. G. Green, V. V. Fokin, and K. B. Sharpless, *Angew. Chem. Int. Ed.,* 2002, 41, 2596–2599).

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and for use as an anti-bacterial agent; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The compositions of the invention may be in a form suitable for oral use (for example as tablets, lozenges, hard or soft capsules, aqueous or oily suspensions, (lipid) emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

A pharmaceutical composition to be dosed intravenously may contain advantageously (for example to enhance stability) a suitable bactericide, antioxidant or reducing agent, or a suitable sequestering agent.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent compounded with an appropriate and convenient amount of excipients which may vary from about 5 to about 98 percent by weight of the total composition. Dosage unit forms will generally contain about 100 mg to about 1 g of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg-$^1$ to 20 mgkg-$^1$ of a compound of this invention, the composition being administered 1 to 4 times per day. In another embodiment a daily dose of 5 mgkg-$^1$ to 20 mgkg-$^1$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

In addition to the compounds of the present invention, the pharmaceutical composition of this invention may also contain (ie through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents. Compounds of this invention may also be co-formulated or co-administered with a vitamin, for example Vitamin B, such as Vitamin B2, Vitamin B6, Vitamin B12 and folic acid. Compounds of the invention may also be formulated or co-administered with cyclooxygenase (COX) inhibitors, particularly COX-2 inhibitors.

In one aspect of the invention, a compound of the invention is co-formulated with an antibacterial agent which is active against gram-positive bacteria.

In another aspect of the invention, a compound of the invention is co-formulated with an antibacterial agent which is active against gram-negative bacteria.

In another aspect of the invention, a compound of the invention is co-administered with an antibacterial agent which is active against gram-positive bacteria.

In another aspect of the invention, a compound of the invention is co-administered with an antibacterial agent which is active against gram-negative bacteria.

In the above other, pharmaceutical composition, process, method, use and medicament manufacture features, the alternative and preferred embodiments of the compounds of the invention described herein also apply.

BIOLOGICAL ACTIVITY

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S. aureus and coagulase negative staphylococci, together with haemophilus and moraxella strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 μg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of $5 \times 10^4$ CFU/well.

For example, the following results were obtained for the compound of Example 1:

| Organism | MIC (μg/ml) |
| --- | --- |
| Staphylococcus aureus: | |
| MSQS | 4 |
| MRQR | 1 |
| Streptococcus pneumoniae | 0.5 |
| Moraxella catarrhalis | 1 |
| Enterococcus faecium | 1 |

MSQS = methicillin sensitive and quinolone sensitive
MRQR = methicillin resistant and quinolone resistant The activity of the compounds of the invention against MAO-A was tested using a standard in-vitro assay based on human liver enzyme expressed in yeast as described in Biochem. Biophys. Res. Commun. 1991, 181, 1084–1088. The compounds of the invention showed decreased MAO-A potency compared with analogues from the known art with C-5 side chains such as acetamidomethyl or unsubstituted azolylmethyl or hydroxymethyl. The compounds of the invention showed decreased MAO-A potency compared with analogues in which the HET group of formula (Ia) to (If) is unsubstituted. When Ki values were measured in such an assay as above, Example 1 showed a Ki value of 21 μg/ml, whereas the unsubstituted triazole equivalent showed a Ki value of 2.4 μg/ml.

Certain intermediates and/or Reference Examples described hereinafter within the scope of the invention may also possess useful activity, and are provided as a further feature of the invention.

The invention is now illustrated but not limited by the following Examples in which unless otherwise stated:—

(i) evaporations were carried out by rotary evaporation under vacuum and work-up procedures were carried out after removal of residual solids by filtration;

(ii) operations were carried out at ambient temperature, that is typically in the range 18–26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Bruker DRX-300 spectrometer operating at a field strength of 300 MHz, or a Bruker DRX-500 spectrometer operating at a field strength of 500 MHz; chemical shifts are reported in parts per million downfield from tetramethysilane as an internal standard (δ(delta) scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected];

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:—

DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; EI is electron impact; CI is chemical ionisation; EtOAc is ethyl acetate; MeOH is methanol.

EXAMPLE 1

(5R)-3-[3-Fluoro-4-(3-methylisoxazol-5-yl)phenyl]-5-[(4-methyl-1H-1,2,3-triazol-1-yl)methyl]-1,3-oxazolidin-2-one

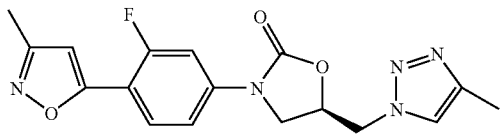

(5R)-3-(3-Fluoro-4-iodophenyl)-5-[(4-methyl-1H-1,2,3-triazol-1-yl)methyl]-1,3-oxazolidin-2-one (Intermediate 2, 2.08 g, 5.20 mmol) was dissolved in anhydrous 1,4-dioxane (10 ml) and degassed and placed under argon. Bis(triphenylphospine)palladium(II) chloride (0.145 g, 0.210 mmol) was added followed by dropwise addition of 5-(tributylstannyl)-3-methylisoxazole (2.41 g, 6.50 mmol) (Sakamoto, T. et al., Tetrahedron, 47, 28, 5111–5118) in 1,4-dioxane (2 ml). The reaction was degassed and heated at 100° C. for 48 hours. The solvent was removed under vacuum and the residue was dissolved in acetonitrile and washed with hexanes. The acetonitrile layer was concentrated to give a yellow solid (1.64 g) that was adsorbed onto silica gel and purified by flash chromatography using 10–20% acetone/dichloromethane. Relevant fractions were concentrated to give an off-white solid (1.50 g).

MS (ESP): 357 ($MH^+$) for $C_{17}H_{16}FN_5O_3$ $^1$H-NMR 500 MHz (DMSO-$d_6$) δ: 2.24 (s, 3H); 2.32 (s, 3H); 3.94–3.97 (m, 1H); 4.30 (t, 1H); 4.98 (d, 2H); 5.14–5.19 (m, 1H); 6.73 (d, 1H); 7.49 (dd, 1H); 7.66 (dd, 1H); 7.98 (s, 1H); 7.94 (t, 1H).

The intermediates for this compound was prepared as follows:

Intermediate 1

(5R)-3-(3-Fluorophenyl)-5-[(4-methyl-1H-1,2,3-triazol-1-yl)methyl]-1,3-oxazolidin-2-one

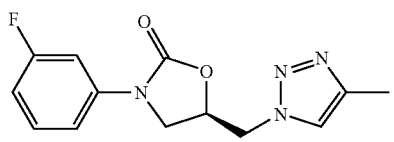

N,N-Diisopropylethylamine (3.20 ml, 18.35 mmol) was added to a solution of (5S)-5-(aminomethyl)-3-(3-fluorophenyl)-1,3-oxazolidin-2-one (0.77 g, 3.57 mmol) (see Patent Application: Dong Pharmaceuticals WO 01/94342) in anhydrous methanol (25 ml). The solution was cooled to 0° C., and N'-[2,2-dichloro-1-methylethylidene]-4-methylbenzenesulfonohydrazide (1.28 g, 4.58 mmol) was added. The solution was warmed to room temperature and stirred overnight. The reaction mixture was then concentrated under vacuum and chromatographed on silica gel using 2% methanol/dichloromethane to give 0.71 g of the title product.

MS (ESP): 277 (M+1) for $C_{13}H_{13}FN_4O_2$ $^1$H-NMR 500 MHz (DMSO-$d_6$) δ: 2.24 (s, 3H); 3.90 (dd, 1H); 4.25 (t, 1H); 4.77 (d, 2H); 5.13 (m, 1H); 6.99 (m, 1H); 7.28 (d, 1H); 7.42–7.48 (m, 2H); 7.89 (s, 1H).

Intermediate 2

(5R)-3-(3-Fluoro-4-iodophenyl)-5-[(4-methyl-1H-1,2,3-triazol-1-yl)methyl]-1,3-oxazolidin-2-one

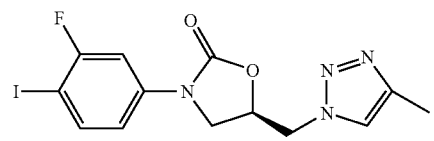

Silver trifluoroacetate (0.52 g, 2.35 mmol) was added to a solution of (5R)-3-(3-fluorophenyl)-5-[(4-methyl-1H-1,2,3-triazol-1-yl)methyl]-1,3-oxazolidin-2-one (Intermediate 1, 0.50 g, 1.81 mmol) in dichloromethane (15 ml). Iodine (0.55 g, 2.17 mmol) was added over 1.5 h, and the reaction mixture was stirred overnight. After 16 h, the solids were removed by filtration and additional silver trifluoroacetate (0.38 g, 1.72 mmol) and iodine (0.27 g, 1.06 mmol) were added. After an additional 24 h, the reaction mixture was filtered. The filter cake was washed with methanol. The methanol filtrate was concentrated under vacuum to give 0.31 g of the title product.

MS (ESP): 403 (M+1) for $C_{13}H_{12}FIN_4O_2$ $^1$H-NMR 500 MHz (DMSO-$d_6$) δ: 2.24 (s, 3H); 3.89 (dd, 1H); 4.23 (t, 1H); 4.76 (d, 2H); 5.12 (m, 1H); 7.17 (dd, 1H); 7.51 (dd, 1H); 7.84 (t, 1H); 7.88 (s, 1H).

EXAMPLE 2

(5R-3-(4-Isoxazol-3-ylphenyl)-5-[(4-methyl-1H-1,2,3-triazol-1-yl)methyl]-1,3-oxazolidin-2-one

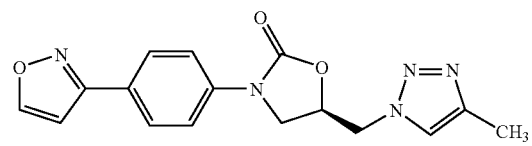

[(5S)-3-(4-Isoxazol-3-ylphenyl)-2-oxo-1,3-oxazolidin-5-yl]methanaminium chloride (Intermediate 8, 288 mg, 0.965 mmol), N'-[(1E)-2,2-dichloro-1-methylethylidene]-4-methylbenzenesulfono-hydrazide (370 mg, 1.25 mmol) and N,N-diisopropylethylamine (1 ml, 5.74 mmol) were added to DMF (5 ml) and the reaction was allowed to stir overnight at room temperature. Ethyl acetate was added (20 ml) and the mixture washed with brine (2×20 ml). The organic layer was dried over $Na_2SO_4$ and then concentrated under vacuum to give a crude residue. The residue was dissolved in DMF (1 ml) and then purified by semi-preprative HPLC. The relevant fractions were lyophilized to yield the product as a white powder (8.8 mg).

MS (ESP): 326.35 (MH+) for $C_{16}H_{15}N_5O_3$ $^1$H-NMR 500 MHz (DMSO-$d_6$) δ: 2.24 (s, 3H); 3.98 (m, 1H); 4.3 (t, 1H); 4.79 (d, 2H); 5.14 (m, 1H); 7.16 (s, 1H); 7.66 (d, 2H); 7.89 (s, 1H); 7.93 (d, 2H); 9.01 (s, 1H).

The intermediates for this compound were prepared as follows:

Intermediate 3

4-Nitrobenzaldehyde oxime

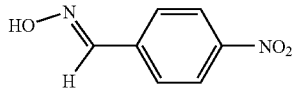

4-Nitrobenzaldehyde (40 g, 264.49 mmol) was added to MeOH (100 ml) followed by hydroxylamine hydrochloride (22.9 g, 330.9 mmol) in $H_2O$ (100 ml). The solution was then cooled to 0° C. Sodium carbonate (16.9 g, 159.5 mmol) in $H_2O$ (100 ml) was added and the reaction was allowed to stir overnight. The MeOH was removed under vacuum and then $H_2O$ (400 ml) was added. The precipitate was filtered and dried under vacuum to yield the product (39.65 g, 238.68 mmol).

$^1$H-NMR 500 MHz (DMSO-$d_6$) δ: 7.87 (d, 2H); 8.27 (d, 2H); 8.33 (s, 1H); 11.87 (s, 1H).

Intermediate 4

3-(4-Nitrophenyl)isoxazole

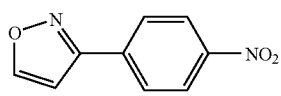

4-Nitrobenzaldehyde oxime (Intermediate 3, 20 g, 120.5 mmol) and bicyclo[2.2.1]hepta-2,5-diene (32.45 ml, 3015.25 mmol) were added to THF (200 ml) followed by dropwise addition of bleach (6.15% NaOCl, 861.5 ml). The reaction was allowed to stir overnight and then the THF and $H_2O$ layers were separated, the THF layer was dried over $Na_2SO_4$ and then concentrated under vacuum. The dried material was added to dioxane and heated to 100° C. for 7 days. The crude material was purified by column chromatography using 5–50% EtOAc in hexanes to yield the final product (10 g).

$^1$H-NMR 500 MHz (DMSO-$d_6$) δ: 7.35 (s, 1H); 8.20 (d, 2H); 8.38 (d, 2H); 9.14 (s, 1).

Intermediate 5

4-Isoxazol-3-ylphenylamine

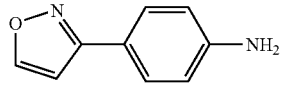

3-(4-Nitrophenyl)isoxazole (Intermediate 4, 8 g, 42 mmol) was added to acetic acid (126 ml) and then $SnCl_2$ (39 g, 205 mmol) in HCl (42 ml) was added. The reaction was allowed to stir for 4 hours and then 1M NaOH was added to bring the solution to pH~11. The water layer was extracted with EtOAc and then the organic layers were collected, dried over $Na_2SO_4$, and dried under vacuum to yield the product (4 g).

$^1$H-NMR 500 MHz (DMSO-$d_6$) δ: 5.56 (s, 2H); 6.47 (d, 2H); 6.93 (s, 1H); 7.55 (d, 2H); 8.87 (s, 1H).

Intermediate 6

Benzyl 4-isoxazol-3-ylphenylcarbamate

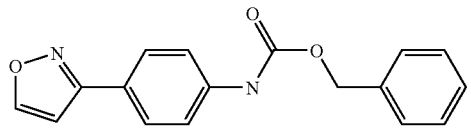

4-Isoxazol-3-ylphenylamine (Intermediate 5, 4 g, 24.69 mmol) was added to dichloromethane (20 ml) followed by pyridine (4.6 ml). The solution was cooled to 0° C. and benzyl chloroformate (5.27 ml, 37.02 mmol) was added drop wise. The solution was allowed to stir for 2 hours at room temperature and then concentrated under vacuum. The residue was added to 30 ml of 1:1 hexane:EtOAc mixture. The crystals were collected by filtration to yield the product (2.26 g).

$^1$H-NMR 500 MHz (DMSO-$d_6$) δ: 5.2 (s, 2H); 6.94 (s, 1H); 7.41 (m, 7H); 7.84 (d, 2H); 8.88 (s, 1H); 10.1 (s, 1H).

Intermediate 7

[(5R)-3-(4-Isoxazol-3-ylphenyl)-2-oxo-1,3-oxazolidin-5-yl]methyl methanesulfonate

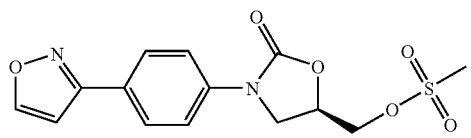

Benzyl 4-isoxazol-3-ylphenylcarbamate (Intermediate 6, 2.26 g, 7.61 mmol) was added to THF and cooled to −78° C. n-Butyl lithium (1.6 M, 5.23 ml, 8.37 mmol) was added.

The mixture was allowed to stir for 30 min and then (R)-(−)-glycidyl butyrate (1.19 ml, 8.37 mmol) was added drop wise. The reaction was allowed to stir overnight warming to room temperature, then methanol (5 ml) was added. Saturated NaHCO$_3$ was then added and the product was extracted into EtOAc. The organic layers were washed with brine, then dried over Na$_2$SO$_4$ and concentrated under vacuum to yield crude product. The crude material was dissolved in EtOAc (10 ml) and hexane (10 ml) and the precipitate was collected by filtration. The resulting ((5R)-5-(hydroxymethyl)-3-(4-isoxazol-3-ylphenyl)-1,3-oxazolidin-2-one (780 mg, 2.98 mmol) was added to CH$_2$Cl$_2$ (10 ml) followed by addition of triethylamine (0.496 ml, 3.58 mmol). The solution was cooled to 0° C., and methanesulfonyl chloride (0.253 ml, 3.27 mmol) was added and the reaction was allowed to stir or 2 hours at 0° C. Brine was added and the mixture extracted with CH$_2$Cl$_2$. The organic layers were collected, dried over Na$_2$SO$_4$ and then concentrated under vacuum to yield the product (400 mg).

$^1$H-NMR 500 MHz (DMSO-d$_6$) δ: 3.28 (s, 3H); 3.91 (t, 1H); 4.27 (t, 1H); 4.52 (m, 2H); 5.06 (m, 1H); 7.16 (s, 1H); 7.39 (d, 2H); 7.96 (d, 2H); 9.01 (s, 1H).

Intermediate 8

[(5S)-3-(4-Isoxazol-3-ylphenyl)-2-oxo-1,3-oxazolidin-5-yl]methanaminium chloride

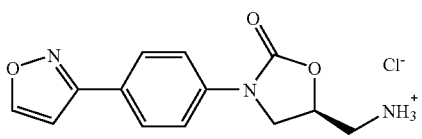

[(5R)-3-(4-Isoxazol-3-ylphenyl)-2-oxo-1,3-oxazolidin-5-yl] methyl methanesulfonate (Intermediate 7,400 mg, 1.18 mmol), sodium azide (99 mg, 1.53 mmol), 18 crown-6 (23.6 mg, 0.089 mmol) and tetrabutylammonium iodide (28.2 mg, 0.076 mmol) were combined in DMF (5 ml) and heated to 60° C. for 4 hours. EtOAc (20 ml) was added and the organic layers were washed with brine (3×20 ml), dried over Na$_2$SO$_4$ and concentrated under vacuum to yield (5R)-5-(azidomethyl)-3-(4-isoxazol-3-ylphenyl)-1,3-oxazolidin-2-one.
(5R)-5-(Azidomethyl)-3-(4-isoxazol-3-ylphenyl)-1,3-oxazolidin-2-one (300 mg, 1.045 mmol) was added to CH$_2$Cl$_2$: MeOH:THF:H$_2$O 10:10:10:2 and then polystyrene triphenylphosphine resin (2650 mg, 4.18 mmol) was added. The reaction was allowed to stir overnight and then the resin was filtered and washed multiple times with dichloromethane and methanol. The filtrate was concentrated in vacuo and then dissolved in dichloromethane (10 ml) followed by addition of 2N HCl in ether (0.5 ml). The precipitate was collected and washed with ether (2×20 ml) and then dried under vacuum to yield the title product (300 mg).

$^1$H-MR 500 MHz (DMSO-d$_6$) δ: 3.29 (t, 1H); 4.04 (m, 2H); 4.3 (m, 1H); 5.16 (m, 1H); 7.17 (s, 1H); 7.71 (d, 2H); 7.96 (d, 2H); 9.02 (s, 1H).

EXAMPLE 3

(5R)-3-[4-(1-Benzyl-1H-1,2,3-triazol-4-yl)-3-fluorophenyl]-5-[(4-methyl-1H-1,2,3-triazol-1-yl)methyl]-1,3-oxazolidin-2-one

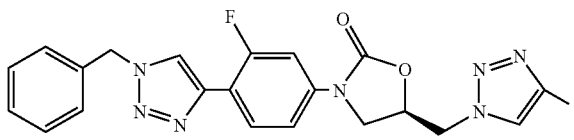

(5R)-3-(4-Ethynyl-3-fluorophenyl)-5-[(4-methyl-1H-1,2,3-triazol-1-yl)methyl]-1,3-oxazolidin-2-one (Intermediate 9, 40 mg, 0.133 mmol), azidomethyl-benzene(21.2 mg, 0.16 mmol), copper iodide (2.5 mg, 0.013 mmol) and 2,6-lutidine were mixed in dry acetonitrile (2 mL) and stirred at room temperature for over night. The reaction mixture was filtered through a 0.45 μm membrane, the filtrate was concentrated to an oil and purified by reverse phase chromatography with 5%~95% MeCN in H$_2$O (0.1% TFA). The product was obtained as a colourless solid (15 mg).

MS (ESP): 434.62 (MH$^+$) for C$_{22}$H$_{20}$FN$_7$O$_2$ $^1$H-NMR 300 MHz (DMSO-d$_6$) δ: 2.22 (s, 3H); 3.90 (dd, 1H); 4.26 (dd, 1H); 4.76 (d, 2H); 5.12 (m, 1H); 5.67 (s, 2H); 7.37 (m, 6H); 7.57 (dd, 1H); 7.87 (s, 1H); 8.11 (dd,1H); 8.46 (d, 1H).

Intermediate 9

(5R)-3-(4-Ethynyl-3-fluorophenyl)-5-[(4-methyl-1H-1,2,3-triazol-1-yl)methyl]-1,3-oxazolidin-2-one

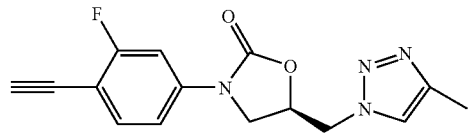

(5R)-3-{3-Fluoro-4-[(trimethylsilyl)ethynyl]phenyl}-5-[(4-methyl-1H-1,2,3-triazol-1-yl)methyl]-1,3-oxazolidin-2-one (Intermediate 10, 1.4 g, 3.76 mmol) was dissolved in methanol (10 ml) and cooled to 0° C. 1N potassium hydroxide aqueous solution (4 mL) was added and the mixture was stirred for one hour. 2M HCl (4 mLl) was added and the reaction mixture was stirred for 30 minutes. It was extracted with dichloromethane (30 mL), the organic phase was concentrated to dryness. The product was precipitated from dichloromethane (10 mL) by the additon of hexanes (50 mL) to give the product as a colourless solid (0.91 g).

MS (ESP): 301.16 (MH$^+$) for C$_{15}$H$_{13}$FN$_4$O$_2$ $^1$H-NMR 300 MHz (DMSO-d$_6$) δ: 2.20 (s, 3H); 3.87 (dd, 1H); 4.22 (dd, 1H); 4.41 (s, 1H); 4.76 (d, 2H); 5.12 (m, 1H); 7.28 (dd, 1H); 7.55 (m, 2H); 7.85 (s, 1H).

Intermediate 10

(5R)-3-{3-Fluoro-4-[(trimethylsilyl)ethynyl]phenyl}-5-[(4-methyl-1H-1,2,3-triazol-1-yl)methyl]-1,3-oxazolidin-2-one

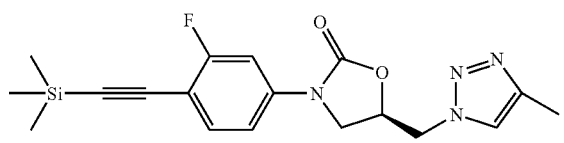

Ethynyl(trimethyl)silane (432 mg, 4.4 mmol), copper iodide (76 mg, 0.4 mmol), triethylamine (2.02 g, 20 mmol) and palladium tetrakis triphenylphosphine (231 mg, 0.2 mmol) were added to a solution of (5R)-3-(3-fluoro-4-iodophenyl)-5-[(4-methyl-1H-1,2,3-triazol-1-yl)methyl]-1,3-oxazolidin-2-one (WO2003072575) (Intermediate 2,1.61 g, 4.0 mmol) in a sealed reaction vessel. The reaction mixture was stirred at 60° C. over night, then cooled down to room temperature and filtered through celite. The filtrate was concentrated and purified by flash chromatography on silica gel with 30% hexanes in ethyl acetate. The product was obtained as a yellowish solid (1.4 g).

MS (ESP): 373.26 (MH$^+$) for $C_{18}H_{21}FN_4O_2Si$ $^1$H-NMR 300 MEW (CDCl$_3$) δ: 0.29 (s, 9H); 2.39 (s, 3H); 3.93 (dd, 1H); 4.22 (dd, 1H); 4.82 (m, 2H); 5.12 (m, 1H); 7.08 (dd, 1H); 7.35–7.55 (m, 2H); 7.65 (s, 1H).

The invention claimed is:

1. A compound of the formula (I), or a pharmaceutically-acceptable salt, or an in-vivo-hydrolysable ester thereof,

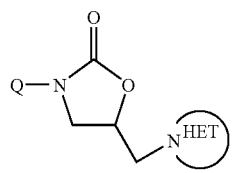
(I)

wherein —N—HET is:

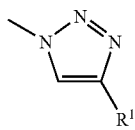
(Id)

wherein
$R^1$ is (1-4C)alkyl;
or $R^1$ is selected from a substituent from the group
($R^1$a) wherein $R^1$ is halogen, hydroxy, (1-4C)alkoxy, (2-4C)alkenyloxy, (2-4C)alkenyl, (2-4C)alkynyl (optionally subsiltuted on the terminal carbon by CH$_2$=CH—, di(1-4C)alkylamino, AR2, AR2a or AR2b, wherein AR2, AR2a and AR2b are defined hereinbelow), (3-6C)cycloalkyl, (3-6C)cycloalkenyl, amino, (1-4C)alkylamino, di-(1-4C)alkylamino, (2-4C)alkenylamino, (1-4C)alkyl-S(O)q- (wherein q is 0, 1 or 2), (1-4C)alkylcarbonylamino,;

or $R^1$ is selected from the group
($R^1$b) wherein $R^1$ is a (1-4C)alkyl group which is substituted by one substituent selected from hydroxy, halo, (1-4C)alkoxy, amino, (1-4C)alkylamino, di(1-4C)alkylamino, cyano, azido, (2-4C)alkenyloxy, (1-4C)alkyl-S(O)q- (wherein q is 0, 1 or 2), AR1-S(O)q- (wherein q is 0, 1 or 2 and AR1 is defined hereinbelow), AR2-S(O)q- (wherein q is 0, 1 or 2), AR2a-S(O)q- (wherein q is 0, 1 or 2), benzyl-S(O)q- (wherein q is 0, 1 or 2), (3-6C)cycloalkyl, (3-6C)cycloalkenyl, (1-40)alkyl-OCO—NH—, (1-4C)alkyl-NHCO—O—, (1-4C)alkylaminocarbonyl, di(1-4C)alkylaminocarbonyl, H$_2$NC(=NH)S—;

or $R^1$ is selected from a group of formula ($R^1$c1):—
($R^1$c1) a fully saturated 4-membered monocyclic ring containing 1 or 2 heteroatoms independently selected from C, N and S (optionally oxidised), and linked via a ring nitrogen or carbon atom; or or $R^1$ is selected from the group
($R^1$d) cyano, nitro, azido, formyl, (1-4C)alkylcarbonyl, (1-4C)alkoxycarbonyl, H$_2$NC(O)—, (1-4)alkylNHC(O)—;

and wherein at each occurrence of an $R^1$ substituent containing an alkyl, alkenyl, alkynyl, cycloalkyl or cycloalkenyl moiety in ($R^1$a), ($R^1$b) or ($R^1$c1) each such moiety is optionally further substituted on an available carbon atom with one, two, three or more substituents independently selected from F, Cl Br, OH and CN;

Q is:

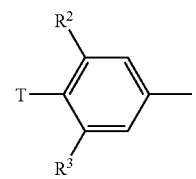
Q1 wherein $R_2$ and $R_3$ are independently selected from H, F, Cl, CF$_3$, OMe, SMe, Me and Et;
wherein T is selected from the groups in (TAa1) to (TAa12):

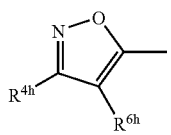
(TAa1)

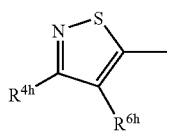
(TAa2)

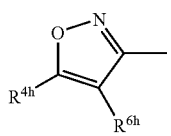
(TAa3)

-continued

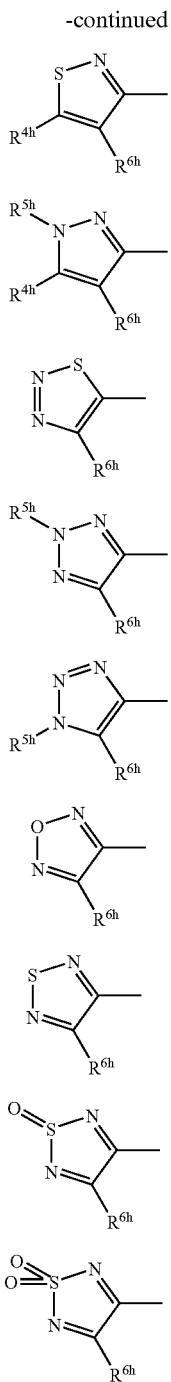

(TAa4)

(TAa5)

(TAa6)

(TAa7)

(TAa8)

(TAa9)

(TAa10)

(TAa11)

(TAa12)

wherein:
$R^{6h}$ is selected from hydrogen, (1-4C)alkyl, (1-4C)alkoxycarbonyl, (1-4C)alkanoyl, carbamoyl and cyano;
$R^{4h}$ and $R^{5h}$ are independently selected from hydrogen, halo, trifluoromethyl, cyano, nitro, (1-4C)alkoxy, (1-4C)alkylS(O)$_q$- (q is 0, 1 or 2), (1-4C)alkanoyl, (1-4C)alkoxycarbonyl, benzyloxy-(1-4C)alkyl, (2-4C)alkanoylamino, —CON RcRv and —NRcRV wherein any (1-4C)alkyl group contained in the preceding values for $R^{4h}$ and $R^{6h}$ is optionally substituted by up to three substituents independently selected from hydroxy (not on C1 of an alkoxy group, and excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$- (q is 0, 1 or 2), (1-4C)alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;

$R^{4h}$ and $R^{5h}$ may further be independently selected from (1-4C)alkyl {optionally substituted by one, two or three substituents independently selected from hydroxy (excluding geminal disubstitution), oxo, trifluoromethyl, cyano, nitro, (1-4C)alkoxy, (2-40)alkanoyloxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], hydroxyimino, (1-4C)alkoxyimino, (1-4C)alkylS(O)$_q$- (q is 0, 1 or 2), (1-4C)alkylSO$_2$—NRV-, (1-4C)alkoxycarbonyl, —CONRcRv, —NRcRv (excluding geminal disibstitution), ORc, and phenyl (optionally substituted by one, two or three substituents independently selected from (1-4C)alkyl, (1-4C)alkoxy and halo)};

wherein Rv is hydrogen or (1-4C)alkyl and Rc is as hereinafter defined; and wherein any (1-4C)alkyl group contained in the immediately preceding optional substituents (when $R^{4h}$ and $R^{5h}$ are independently (1-4C)alkyl) is itself optionally substituted by up to three substituents independently selected from hydroxy (not on C1 of an alkoxy group, and excluding geminal disubstitution), oxo, trifluoromethyl, cyano, nitro, (1-4) alkoxy, (2-4C)alkanoyloxy, hydroxyimino, (1-4C) alkoxyimino, (1-4C)alkylS(O)$_q$- (q is 0, 1 or 2), (1-4C) alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;

or $R^4$ is selected from one of the groups in (TAaa) to (TAab) below, or (where appropriate) one of $R^{4h}$ and $R^{5h}$ is selected from the above list of Rdh$^{4h}$ and $R^{5h}$ values, and the other is selected from one of the groups in (TAaa) to (TAab) below:—(TAaa) a group of the formula (TAaa1)

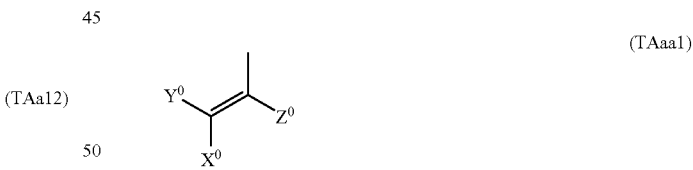

(TAaa1)

wherein $Z^0$ is hydrogen or (1-4C)alkyl;
$X^0$ and $Y^0$ are independently selected from hydrogen, (1-4C)alkyl, (1-4C)alkoxycarbonyl, halo, cyano, nitro, (1-4C)alkylS(O)$_q$- (q is 0, 1 or 2), RvRwNSO$_2$-, trifluoromethyl, pentafluoroethyl, (1-4C)alkancayl and —CONRvRw [wherein Rv is hydrogen or (1-4C)alkyl; Rw is hydrogen or (1-4C)alkyl];
(TAab) an acetylene of the formula -≡-H or -≡-(1-4C) alkyl;
wherein Rc is selected from groups (Rc1) to (Rc2):—
(Rc1) (1-6C)alkyl {optionally substituted by one or more (1-4C)alkanoyl groups (including geminal disubstitution) and/or optionally monosubstituted by cyano, (1-4C)alkoxy, trifluoromethyl, (1-4C)alkoxycarbonyl, phenyl (optionally substituted as for AR1 defined hereinafter), (1-4C)alkylS(O)$_q$- (q is 0, 1 or 2); or, on any but the first carbon atom of the (1-6C)alkyl chain, optionally substituted by one or more groups (including geminal disubstitution) each independently selected from hydroxy and fluoro, and/or optionally monosubstituted by oxo, —NRvRw [wherein Rv is hydrogen or (1-4C)alkyl; Rw is hydrogen or (1-4C)alkyl], (1-6C)alkanoylamino, (1-4C)alkoxycarbonylamino, N-(1-4C)alkyl-N-(1-6C)alkanoylamino, (1-4C)alkylS(O)$_p$NH— or (1-4C)alkylS(O)$_p$-((1-4C)alkyl)N— (p is 1 or 2))};

(Rc2) R$^{13}$CO—, R$^{13}$SO$_2$— or R$^{13}$CS— wherein R$^{13}$ is selected from (Rc2a) to (Rc2d):—(Rc2a) hydrogen, (1-4C)alkoxycarbonyl, trifluoromethyl and —NRvRw [wherein Rv is hydrogen or (1-4C)alkyl; Rw is hydrogen or (1-4C)alkyl];

(Rc2b) (1-10C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C) alkoxy-(1-4C)alkoxy, (1-4C)alkanoyl, carboxy, phosphoryl [—O—P(O)(OH)$_2$, and mono- and di-(1-4C) alkoxy derivatives thereof], phosphiryl [—O—P(OH)$_2$ and mono- and di-(1-4C)alkoxy derivatives thereof], and amino; and/or optionally substituted by one group selected from phosphonate [phosphono, —P(O)(OH)$_2$, and mono- and di-(1-4C)alkoxy derivatives thereof], phosphinate [—P(OH)$_2$ and mono- and di-(1-4C) alkoxy derivatives thereof], cyano, halo, trifluoromethyl, (1-4C)alkoxycarbonyl, (1-4C) alkoxy-(1-4C) alkoxycarbonyl, (1-4C)alkoxy-(1-4C)alkoxy-(1-4C) alkoxycarbonyl, (1-4C)alkylamino, di((1-4C)alkyl) amino, (1-6C)alkanoylamino, (1-4C)alkoxycarbonylamino, N-(1-4C)alkyl-N-(1-6C)alkanoylamino, (1-4C)alkylaminocarbonyl, di((1-4C) alkyl)aminocarbonyl, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$- [the (1-4C)alkyl group of (1-4C)alkylS(O)$_q$- being optionally substituted by one substituent selected from hydroxy, (1-4C)alkoxy, (1-4C)alkanoyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], amino, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, carboxy, (1-4C)alkylamino, di((1-4C)alkyl) amino, (1-6C)alkanoylamino, (1-4C)alkoxycarbonylamino, N-(1-4C)alkyl-N-(1-6C)alkanoylamino, (1-4C)alky aminocarbonyl, di((1-4C)alkyl)aminocarbonyl, (1-4C)alkylS(O)$_p$NH—, (1-4C)alkylS(O)$_p$-((1-4C)alkyl)N—, and (1-4C)alkylS(O)$_q$-;

(Rc2C)R$^{14}$C(O)O(1-6C)alkyl wherein R$^{14}$ is AR1, AR2, (1-4C)alkylamino (the (1-4C)alkyl group being optionally substituted by (1-4C)alkoxycarbonyl or by carboxy), benzyloxy-(1-4C)alkyl or (1-10C)alkyl {optionally substituted as defined for (Rc2b)};

(Rc2d) R$^{15}$O— wherein R$^{15}$ is benzyl, (1-6C)alkyl {optionally substituted as defined for (Rc2c)} or AR2b;

wherein
AR1 is an optionally substituted phenyl or optionally substituted naphthyl;
AR2 is an optionally substituted 5- or 6-membered, fully unsaturated monocyclic heteroaryl ring containing up to four heteroatoms independently selected from O, N and S (but not containing any O—O, O—S, or S—S bonds), and linked via a ring carbon atom, or a ring nitrogen atom if the ring is not thereby quaternised;
AR2a is a partially hydrogenated version of AR2, linked via a ring carbon atom or linked via a ring nitrogen atom if the ring is not thereby quaternised;
AR2b is a fully hydrogenated version of AR2, linked via a ring carbon atom or linked via a ring nitrogen atom.

2. The compound of claim 1, wherein R$^2$ and R$^3$ are independently hydrogen or fluoro.

3. The compound of claim 1, wherein T is selected from TAa1, TAa5, TAa7 and TAa8.

4. The compound of claim 1, wherein R$^1$ is selected from R$^1$a, R$^1$b, R$^1$c, and R$^1$d.

5. The compound of claim 1, which is a compound of the formula

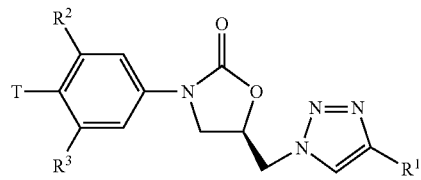

wherein
R$^1$ is (1-4C)alkyl;
R$^2$ and R$^3$ are independently hydrogen or fluoro; and
T is selected from TAa1, TAa5 TAa7 and TAa8.

6. A method for producing an antibacterial effect in a warm blooded animal which comprises administering to said animal an effective amount of a compound of claim 1.

7. A pharmaceutical composition which comprises a compound of claim 1, and a pharmaceutically-acceptable diluent or carrier.

8. A compound which is:
(5R)-3-[3-Fluoro-4-(3-methylisoxazol-5-yl)phenyl]-5-[(4-methyl-1H-1,2,3,-triazol-1-yl)methyl]-1,3-oxazolidin-2-one;
(5R)-3-(4-isoxazol-3-ylphenyl)-5-[(4-methyl-1H-1,2,3-triazol-1-yl)methyl]-1,3-oxazolidin-2-one; or
(5R)-3-[4-(1-Benzyl-1H-1,2,3-triazol-4-yl)-3-fluorophenyl]-5-[(4-methyl-1H-1,2,3-triazol-1-yl)methyl]-1,3-oxazolidin-2-one.

* * * * *